(12) United States Patent
Alaoui-Jamali et al.

(10) Patent No.: US 10,711,002 B2
(45) Date of Patent: Jul. 14, 2020

(54) PURINE COMPOUNDS AND METHOD FOR THE TREATMENT OF CANCER

(71) Applicant: THE ROYAL INSTITUTION FOR THE ADVANCEMENT OF LEARNING/MCGILL UNIVERSITY, Montreal (CA)

(72) Inventors: Moulay A. Alaoui-Jamali, Outremont (CA); Krikor Bijian, Laval (CA); Dominik Wernic, Montréal (CA)

(73) Assignee: THE ROYAL INSTITUTION FOR THE ADVANCEMENT OF LEARNING/MCGILL UNIVERSITY, Montréal (CA)

(*) Notice: Subject to any disclaimer, the term of this patent is extended or adjusted under 35 U.S.C. 154(b) by 0 days.

(21) Appl. No.: 16/094,652

(22) PCT Filed: Apr. 21, 2017

(86) PCT No.: PCT/CA2017/050492
§ 371 (c)(1),
(2) Date: Oct. 18, 2018

(87) PCT Pub. No.: WO2017/181285
PCT Pub. Date: Oct. 26, 2017

(65) Prior Publication Data
US 2019/0119279 A1    Apr. 25, 2019

Related U.S. Application Data

(60) Provisional application No. 62/325,570, filed on Apr. 21, 2016.

(51) Int. Cl.
| | | |
|---|---|---|
| C07D 473/16 | (2006.01) | |
| A61P 35/02 | (2006.01) | |
| A61P 35/04 | (2006.01) | |
| A61K 45/06 | (2006.01) | |
| A61K 31/52 | (2006.01) | |

(52) U.S. Cl.
CPC ............ *C07D 473/16* (2013.01); *A61K 31/52* (2013.01); *A61K 45/06* (2013.01); *A61P 35/02* (2018.01)

(58) Field of Classification Search
CPC ........................... C07D 473/06; C07D 473/16
See application file for complete search history.

(56) References Cited

U.S. PATENT DOCUMENTS 8,258,144 B2    9/2012    Song et al.

FOREIGN PATENT DOCUMENTS

| CN | 106279145 | 1/2017 |
| FR | 0301915 | 4/2008 |
| WO | 0109134 | 2/2001 |
| WO | 0400309 | 12/2003 |
| WO | 2010111406 | 9/2010 |

OTHER PUBLICATIONS

Cancer Drug Design and Discovery, Neidle, Stephen,ed. (Elsevier/Academic Press), pp. 427-431 (2008). (Year: 2008).*
Damodaran et al. Trends in Pharmacological Sciences, Aug. 2017, vol. 38, No. 8 p. 687-700. (Year: 2017).*
Huynh et al. PLoS ONE vol. 6 (5) p. 1-9. (Year: 2011).*
Luistro, L. et al. "Preclinical profile of a potent gamma-secretase inhibitor targeting notch signaling with in vivo efficacy and pharmacodynamic properties". Cancer Res 2009, 69(19). pp. 7672-7680.
Mani, S.A. et al. "The epithelial-mesenchymal transition generates cells with properties of stem cells". Cell 2008, 133(4). pp. 704-715.
McCarthy, N. "Cancer stem cells: Tracing clones". Nature reviews Cancer 2012, 12(9). pp. 579.
Morabito, A. et al. "Vandetanib (ZD6474), a dual inhibitor of vascular endothelial growth factor receptor (VEGFR) and epidermal growth factor receptor (EGFR) tyrosine kinases: current status and future directions". The Oncologist 2009, 14(4). pp. 378-390.
Pantel, K. and Woelfle, U. "Micrometastasis in breast cancer and other solid tumors". Journal of biological regulators and homeostatic agents 2004, 18(2). pp. 120-125.
Pece, S. et al. "Biological and molecular heterogeneity of breast cancers correlates with their cancer stem cell content". Cell 2010, 140(1). pp. 62-73.
Ricardo, S. et al. "Breast cancer stem cell markers CD44, CD24 and ALDH1: expression distribution within intrinsic molecular subtype". Journal of Clinical Pathology 2011, 64(11). pp. 937-946.
Santaguida, S. et al. "Dissecting the role of MPS1 in chromosome biorientation and the spindle checkpoint through the small molecule inhibitor reversine". The Journal of Cell Biology 2010, 190(1). pp. 73-87.

(Continued)

*Primary Examiner* — Emily A Bernhardt
(74) *Attorney, Agent, or Firm* — Norton Rose Fulbright Canada LLP

(57) ABSTRACT

The present disclosure relates to novel compound of Formula I, or a pharmaceutically acceptable salt or solvate thereof; wherein $R_1$, $R_2$, Ra, Rb and Rc are as defined herein, pharmaceutical compositions containing same and methods for the treatment of cancer using same.

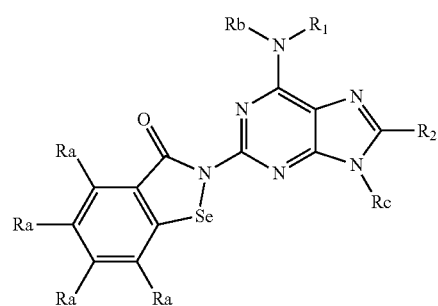

16 Claims, 4 Drawing Sheets

(56) References Cited

OTHER PUBLICATIONS

Seton-Rogers, S. "Metastasis: dynamic interactions". Nature Reviews Cancer 2012, 12(6). pp. 378.

Slack-Davis, J.K. et al. "Cellular characterization of a novel focal adhesion kinase inhibitor". Journal of Biological Chemistry 2007, 282(20). pp. 14845-14852.

Valent, P. et al. "Cancer stem cell definitions and terminology: the devil is in the details". Nature Reviews Cancer 2012, 12(11). pp. 767-775.

Yakes, F.M. et al. "Cabozantinib (XL184), a novel MET and VEGFR2 inhibitor, simultaneously suppresses metastasis, angiogenesis, and tumor growth". Molecular Cancer Therapeutics 2011, 10(12). pp. 2298-2308.

Zhao, B. et al. "Modulation of kinase-inhibitor interactions by auxiliary protein binding: crystallography studies on Aurora A interactions with VX-680 and with TPX2". Protein science : a publication of the Protein Society 2008, 17(10). pp. 1791-1797.

Ackland, M.L. et al. "PMC42, a novel model for the differentiated human breast". Exp Cell Res 2001, 263(1). pp. 14-22.

Al-Hajj, M. "Prospective identification of tumorigenic breast cancer cells". Proceedings of the National Academy of Sciences 2003, 100(7). pp. 3983-3988.

Blick, T. et al. "Epithelial mesenchymal transition traits in human breast cancer cell lines parallel the CD44(hi/)CD24 (lo/-) stem cell phenotype in human breast cancer". Journal of mammary gland biology and neoplasia 2010, 15(2). pp. 235-252.

Chen, B. et al. "Small molecule—mediated disruption of Wnt-dependent signaling in tissue regeneration and cancer". Nature chemical biology 2009, 5(2). pp. 100-107.

Chen, S. et al. "Reversine increases the plasticity of lineage-committed mammalian cells". Proceedings of the National Academy of Sciences 2007, 104(25). pp. 10482-10487.

Favata, M.F. et al. "Identification of a novel inhibitor of mitogen-activated protein kinase kinase". Journal of Biological Chemistry 1998, 273(29). pp. 18623-18632.

Ginestier, C. et al. "ALDH1 is a marker of normal and malignant human mammary stem cells and a predictor of poor clinical outcome". Cell stem cell 2007, 1(5). pp. 555-567.

Grimshaw, M.J. et al. "Mammosphere culture of metastatic breast cancer cells enriches for tumorigenic breast cancer cells". Breast cancer research : BCR 2008, 10(3): R52.

Gupta, P.B. et al. "Identification of selective inhibitors of cancer stem cells by high-throughput screening". Cell 2009, 138(4). pp. 645-659.

Holzel, M. et al. "Plasticity of tumour and immune cells: a source of heterogeneity and a cause for therapy resistance?" Nature reviews Cancer 2013, 13(5). pp. 365-376.

Kloc, K. et al. "Synthesis of 7-Azabenzisoselenazol-3(2H)-ones: A New Group of Selenium Containing Antimicrobials". Synthetic Communications. vol. 33, No. 21, 2003. pp. 3805-3815.

Krause, D.S. and Crispino, J.D. "Molecular pathways: induction of polyploidy as a novel differentiation therapy for leukemia". Clinical cancer research: an official journal of the American Association for Cancer Research 2013, 19(22). pp. 6084-6088.

\* cited by examiner

PURINE COMPOUNDS AND METHOD FOR THE TREATMENT OF CANCER

The present application is the 371 national phase entry of PCT/CA2017/050492 filed Apr. 21, 2017, the content of which is hereby incorporated in its entirety. The present application also claims priority from U.S. provisional patent application Ser. No. 62/325,570, filed 21 Apr. 2016, and entitled "PURINE COMPOUNDS AND METHOD FOR THE TREATMENT OF CANCER", the disclosure of which is hereby incorporated by reference in its entirety.

FIELD OF THE DISCLOSURE

The present disclosure relates to novel compounds, pharmaceutical compositions containing same and methods for the treatment of cancer using same.

BACKGROUND OF THE DISCLOSURE

A broad group of diseases involving unregulated cell growth is known as cancer or as malignant neoplasia. In cancer, cells divide and grow uncontrollably, causing the cells to form lumps or tumors. The cancer may also spread to more distant parts of the body through the lymphatic system or bloodstream. Not all tumors are cancerous; benign tumors do not invade neighboring tissues and do not spread throughout the body.

Metastatic cancer is a prevalent disease and a major cause of cancer-related deaths amongst cancer patients. At present, most non-operable advanced metastatic cancers are considered incurable and search for alternative therapeutic options is currently at the forefront of drug discovery research.

Metastasis is a regulated process involving a rare genetically programmed cancer cell variant with intrinsic invasive capacity. Studies have identified such rare metastatic cell populations to be enriched in specific biomarkers, including cell surface receptors that are often seen in stem cell/progenitor cells. These cell variants are interchangeably referred to as tumor-initiating cells with stem cell-like properties, cancer stem-like cells or cancer stem cells (CSC). In many instances, these tumor-initiating cells with stem cell-like properties have been correlated with cancer heterogeneity, poor prognosis and also found as the culprit to building resistance to many current chemo- and radiation therapies, which ultimately fail since they are not able to eliminate these cells.

For the treatment of cancer, chemotherapeutic, immunotherapeutic or immunomodulatory and antiangiogenic agents have been reported. Agents can be used as monotherapy (treatment with one agent) or as combination therapy (simultaneous, separate or sequential treatment with another agent). The treatments may also be combined with radiotherapy.

SUMMARY OF THE DISCLOSURE

In one aspect, there is provided a compound of formula

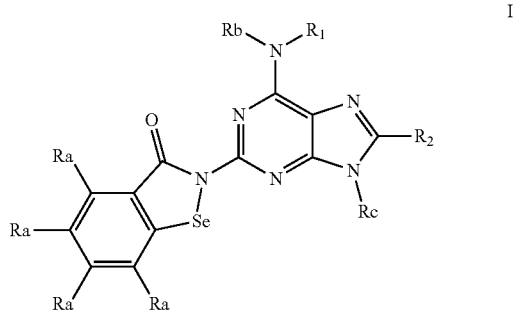

or a pharmaceutically acceptable salt or solvate thereof; wherein $R_1$, $R_2$, Ra, Rb and Rc are as defined herein.

In another aspect of the disclosure, there is provided a pharmaceutical composition comprising a compound as defined herein or a pharmaceutically acceptable salt or solvate thereof, and one or more pharmaceutically acceptable carrier and/or excipient.

In one aspect, there is provided a method, composition, use or combination for reducing or inhibiting metastasis of metastatic cells, comprising administering to a patient in need thereof a therapeutically effective amount of a compound or a pharmaceutically acceptable salt thereof, as defined herein.

In one aspect, there is provided a method, composition, use or combination for treating a cancer, comprising administering to a patient in need thereof a therapeutically effective amount of a compound or a pharmaceutically acceptable salt thereof as defined herein.

In one aspect, there is provided a method, composition or use for treating cancer comprising administering to a patient in need thereof a compound as defined herein and an additional anticancer drug.

In one aspect, there is provided a method, composition, use or combination for reducing or stopping the proliferation of cancer cells comprising administering to a patient in need thereof a therapeutically effective amount of a compound or a pharmaceutically acceptable salt thereof as defined herein.

In one aspect, there is provided a method, composition, use or combination for reducing or stopping the proliferation of cancer cells comprising administering to a patient in need thereof a therapeutically effective amount of a compound or a pharmaceutically acceptable salt thereof as defined herein. and an additional drug useful for reducing or stopping the proliferation of cancer cells.

BRIEF DESCRIPTION OF THE DRAWINGS

FIG. 1A is a photograph and FIG. 1B is a bar graph that represent the number of mammosphere while

DESCRIPTION OF THE EMBODIMENTS

Figure 1A:
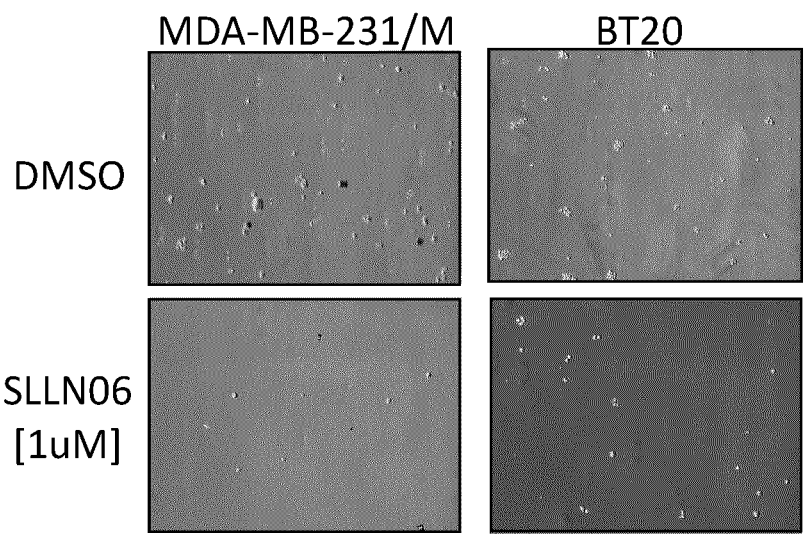

In accordance with one embodiment, there is provided a compound of formula

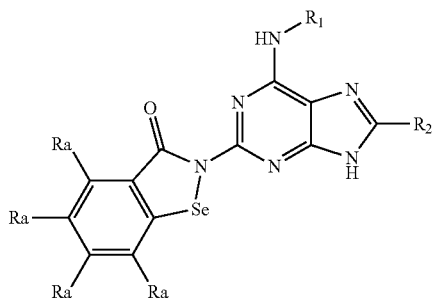

II or a pharmaceutically acceptable salt or solvate thereof; wherein $R_1$, $R_2$, and Ra are as defined herein.

In accordance with a further embodiment, there is provided a compound of formula

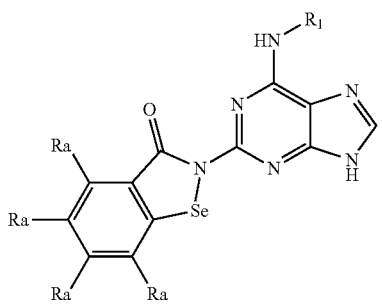

III or a pharmaceutically acceptable salt or solvate thereof, wherein $R_1$, and Ra are as defined herein.

In one embodiment, each Ra is independently H, a straight or branched alkyl, lower cycloalkyl, straight or branched alkoxy, heteroaryl or halogen.

In one embodiment, each Ra is independently H, a lower straight or branched alkyl, lower cycloalkyl, lower straight or branched alkoxy, heteroaryl of 5-6 members or halogen.

In one embodiment, each Ra is independently H, a straight alkyl of 1-3 carbon atoms, or branched alkyl of 3 carbon atoms, straight alkoxy of 1-3 carbon atoms or branched alkoxy of 3 carbon atoms, cycloalkyl of 3 carbon atoms, heteroaryl of 5-6 members or fluoride atom.

In one embodiment, each Ra is independently H, a straight alkyl or fluoroalkyl of 1-3 carbon atoms; branched alkyl or fluoroalkyl of 3 carbon atoms; straight alkoxy or fluoroalkoxy of 1-3 carbon atoms; branched alkoxy or fluoroalkoxy of 3 carbon atoms, cycloalkyl of 3 carbon atoms, heteroaryl of 5-6 members or fluoride atom.

In one embodiment, each Ra is independently H, methyl, ethyl, n-propyl, isopropyl, n-butyl, sec-butyl, ter-butyl, trifluoromethyl, trifluoromethoxy, methoxy, cyclopropyl, cyclobutyl, cyclopentyl cyclohexyl, heteroaryl of 5-6 members comprising at least one heteroatom selected from oxygen (O), and nitrogen (N); or fluoride atom.

In one embodiment, each Ra is independently H, methyl, ethyl, n-propyl, isopropyl, n-butyl, sec-butyl, ter-butyl, trifluoromethyl, trifluoromethoxy, methoxy, or fluoride atom.

In one embodiment, Rb is H or a lower straight or branched alkyl. In a further embodiment, Rb is H or methyl, ethyl, n-propyl, isopropyl. In a further embodiment, Rb is H.

In one embodiment, Rc is H or a lower straight or branched alkyl. In a further embodiment, Rc is H or methyl, ethyl, n-propyl, isopropyl or trifloromethyl. In a further embodiment, Rc is H.

In one embodiment, R1 is a selenium-containing heterocycle, a bridged bicycloalkyl, or a straight or branched alkyl, cycloalkyl, aryl, heterocycle or heteroaryl.

In one embodiment, R1 is straight or branched alkyl, cycloalkyl, aryl, heterocycle or heteroaryl.

In a further embodiment, R1 is straight or branched alkyl of 1 to 10 carbon atoms, cycloalkyl of 3 to 10 carbon atoms, aryl of 6 to 10 carbon atoms, heterocycle of 3-10 members or heteroaryl of 6-10 members. In a further embodiment, R1 is straight or branched alkyl of 3 to 10 carbon atoms, cycloalkyl of 3 to 7 carbon atoms, aryl of 6 to 10 carbon atoms, heterocycle of 5-10 members or heteroaryl of 6-10 members. In a further embodiment, R1 is straight or branched alkyl of 3 to 6 carbon atoms, cycloalkyl of 6 or 7 carbon atoms, aryl of 6 carbon atoms, heterocycle of 5 or 6 members or heteroaryl of 5 or 6 members. In one embodiment, R1 is cycloalkyl or heterocycle. In a further embodiment, R1 is cycloalkyl. In a further embodiment, R1 is heterocycle. In a further embodiment, R1 is cycloalkyl of 6 or 7 carbon atoms or heterocycle of 5 or 6 members. In a further embodiment, R1 is cycloalkyl of 6 or 7 carbon atoms. In a further embodiment, R1 is heterocycle of 5 or 6 members.

In one embodiment, R1 is a selenium-containing heterocycle. In one embodiment, R1 is an optionally substituted 5 or 6 or 7 membered selenium-containing heterocycle. In one embodiment, the selenium-containing heterocycle is

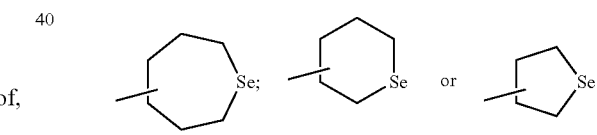

wherein the bond is attached to any available carbon atom.

In one embodiment, the selenium-containing heterocycle is

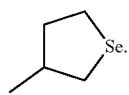

In one embodiment, R1 is a an optionally substituted bridged bicycloalkyl, said bicycloalkyl is a bicyclo[2,2,1] heptyl or bicyclo[3,1,1] heptyl.

In one embodiment, R1 is

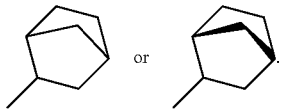

In one embodiment, R1 is

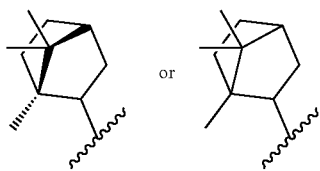

In one embodiment, R1 is

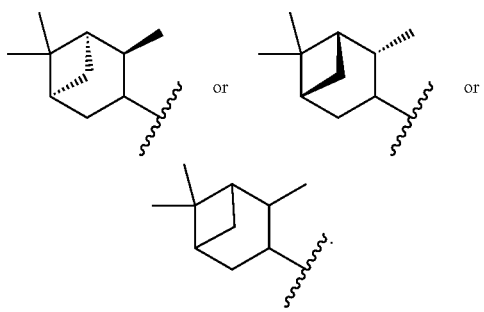

In one embodiment, R2 is H, halogen, alkyl, —S-Rm wherein Rm is selected from alkyl, aryl, -alkylaryl, -alkyl-heterocycle or heterocycle, —NRxRw wherein Rx is H or alkyl and Rw is selected from H, alkyl, aryl, -alkylaryl or heterocycle, or Rx and Rw are taken together with the nitrogen atom to which they are attached to form a heterocycle.

In one embodiment, R2 is H, halogen, alkyl of 1 to 6 carbon atoms, —S-Rm wherein Rm is selected from C1-6alkyl, C6-10aryl, —C1-6alkylC6-10aryl, —C1-6alkyl-3-10 membered heterocycle or 3-10 membered heterocycle, —NRxRw wherein Rx is H or C1-6alkyl and Rw is selected from H, C1-6alkyl, C6-10aryl, —C1-6alkylC6-10aryl or 3-10 membered heterocycle, or Rx and Rw are taken together with the nitrogen atom to which they are attached to form a 3 to 10 membered heterocycle.

In one embodiment, R2 is H, halogen, C1-3alkyl, —NRxRw wherein Rx is H or C1-3alkyl and Rw is selected from H, C1-3alkyl, —C1-3alkylC6aryl or Rx and Rw are taken together with the nitrogen atom to which they are attached to form a 5 or 6 membered heterocycle. In a further embodiment, R2 is H, F, Cl, Br, methyl, ethyl, propyl, isopropyl, —NRxRw wherein Rx is H, methyl or ethyl, and Rw is H, methyl, ethyl, propyl, isopropyl or benzyl or Rx and Rw are taken together with the nitrogen atom to which they are attached to form a piperazinyl, morpholinyl or piperidinyl. In a further embodiment, R2 is H, Cl, methyl, —NH(Me), —N(Me)$_2$, —NH(ethyl), —N(ethyl)$_2$, —NH(propyl), —NH(benzyl) or R2 is —NRxRw wherein Rx and Rw are taken together with the nitrogen atom to which they are attached to form a piperazinyl, morpholinyl or piperidinyl.

In one embodiment, R2 is H, or —NRxRw wherein Rx and Rw are taken together with the nitrogen atom to which they are attached to form a piperazinyl, morpholinyl or piperidinyl. In a further embodiment, R2 is H. In a further embodiment, R2 is —NRxRw wherein Rx and Rw are taken together with the nitrogen atom to which they are attached to form a piperazinyl, morpholinyl or piperidinyl. In a further embodiment, R2 is —NH(Me), —N(Me)$_2$, —NH(ethyl), —N(ethyl)$_2$, —NH(propyl), or —NH(benzyl).

In one embodiment, each Ra is independently H, a straight or branched alkyl, lower cycloalkyl, straight or branched alkoxy, heteroaryl or halogen; Rb is H or a lower straight or branched alkyl; Rc is H or a lower straight or branched alkyl; R1 is an optionally substituted selenium-containing heterocycle, an optionally substituted bridged bicycloalkyl, or an optionally substituted straight or branched alkyl, an optionally substituted cycloalkyl, an optionally substituted aryl, an optionally substituted heterocycle or an optionally substituted heteroaryl; R2 is H, halogen, alkyl, —S-Rm wherein Rm is selected from alkyl, aryl, -alkylaryl, -alkyl-heterocycle or heterocycle, —NRxRw wherein Rx is H or alkyl and Rw is selected from H, alkyl, aryl, -alkylaryl or heterocycle, or Rx and Rw are taken together with the nitrogen atom to which they are attached to form a heterocycle.

In one embodiment, each Ra is independently H, a straight or branched alkyl, lower cycloalkyl, straight or branched alkoxy, heteroaryl or halogen; Rb is H or a lower straight or branched alkyl; Rc is H or a lower straight or branched alkyl; R1 is an optionally substituted selenium-containing heterocycle, or an optionally substituted bridged bicycloalkyl; R2 is H, halogen, alkyl, —S-Rm wherein Rm is selected from alkyl, aryl, -alkylaryl, -alkyl-heterocycle or heterocycle, —NRxRw wherein Rx is H or alkyl and Rw is selected from H, alkyl, aryl, -alkylaryl or heterocycle, or Rx and Rw are taken together with the nitrogen atom to which they are attached to form a heterocycle.

In one embodiment, each Ra is independently H, a straight or branched alkyl, lower cycloalkyl, straight or branched alkoxy, heteroaryl or halogen; Rb is H or a lower straight or branched alkyl; Rc is H or a lower straight or branched alkyl; R1 is straight or branched alkyl, cycloalkyl, aryl, heterocycle or heteroaryl; R2 is H, halogen, alkyl, —S-Rm wherein Rm is selected from alkyl, aryl, -alkylaryl, -alkyl-heterocycle or heterocycle, —NRxRw wherein Rx is H or alkyl and Rw is selected from H, alkyl, aryl, -alkylaryl or heterocycle, or Rx and Rw are taken together with the nitrogen atom to which they are attached to form a heterocycle.

In one embodiment, each Ra is independently H, a straight alkyl of 1-3 carbon atoms, or branched alkyl of 3 carbon atoms, straight alkoxy of 1-3 carbon atoms or branched alkoxy of 3 carbon atoms, cycloalkyl of 3 carbon atoms, heteroaryl of 5-6 members or fluoride atom; Rb is H or methyl, ethyl, n-propyl, isopropyl; Rc is H or methyl, ethyl, n-propyl, isopropyl or trifloromethyl; R1 is straight or branched alkyl of 1 to 10 carbon atoms, cycloalkyl of 3 to 10 carbon atoms, aryl of 6 to 10 carbon atoms, heterocycle of 3-10 members or heteroaryl of 6-10 members; R2 is H, halogen, alkyl of 1 to 6 carbon atoms, —S-Rm wherein Rm is selected from C1-6alkyl, C6-10aryl, —C1-6alkylC6-10aryl, —C1-6alkyl-3-10 membered heterocycle or 3-10 membered heterocycle, —NRxRw wherein Rx is H or C1-6alkyl and Rw is selected from H, C1-6alkyl, C6-10aryl, —C1-6alkylC6-10aryl or 3-10 membered heterocycle, or Rx and Rw are taken together with the nitrogen atom to which they are attached to form a 3 to 10 membered heterocycle.

In one embodiment, each Ra is independently H, methyl, ethyl, n-propyl, isopropyl, n-butyl, sec-butyl, ter-butyl, trifluoromethyl, trifluoromethoxy, methoxy, cyclopropyl, cyclobutyl, cyclopentyl cyclohexyl, heteroaryl of 5-6 members comprising at least one heteroatom selected from oxygen (O), and nitrogen (N); or fluoride atom; Rb is H; Rc is H; R1 is an optionally substituted selenium-containing heterocycle, an optionally substituted bridged bicycloalkyl straight or an optionally substituted branched alkyl of 3 to 6 carbon atoms, an optionally substituted cycloalkyl of 6 or 7 carbon atoms, an optionally substituted aryl of 6 carbon atoms, an optionally substituted heterocycle of 5 or 6 members or an optionally substituted heteroaryl of 5 or 6 members; R2 is H, Cl, methyl, —NH(Me), —N(Me)$_2$, —NH(ethyl), —N(ethyl)$_2$, —NH(propyl), —NH(benzyl) or R2 is —NRxRw wherein Rx and Rw are taken together with the nitrogen atom to which they are attached to form a piperazinyl, morpholinyl or piperidinyl.

In one embodiment, each Ra is independently H, methyl, ethyl, n-propyl, isopropyl, n-butyl, sec-butyl, ter-butyl, trifluoromethyl, trifluoromethoxy, methoxy, cyclopropyl, cyclobutyl, cyclopentyl cyclohexyl, heteroaryl of 5-6 members comprising at least one heteroatom selected from oxygen (O), and nitrogen (N); or fluoride atom; Rb is H; Rc is H; R1 is an optionally substituted selenium-containing heterocycle of 5 or 6 members; R2 is H, Cl, methyl, —NH(Me), —N(Me)$_2$, —NH(ethyl), —N(ethyl)$_2$, —NH(propyl), —NH(benzyl) or R2 is —NRxRw wherein Rx and Rw are taken together with the nitrogen atom to which they are attached to form a piperazinyl, morpholinyl or piperidinyl.

In one embodiment, each Ra is independently H, methyl, ethyl, n-propyl, isopropyl, n-butyl, sec-butyl, ter-butyl, trifluoromethyl, trifluoromethoxy, methoxy, cyclopropyl, cyclobutyl, cyclopentyl cyclohexyl, heteroaryl of 5-6 members comprising at least one heteroatom selected from oxygen (O), and nitrogen (N); or fluoride atom; Rb is H; Rc is H; R1 is an optionally substituted bridged bicycloalkyl of 7 or 8 carbon atoms; R2 is H, Cl, methyl, —NH(Me), —N(Me)$_2$, —NH(ethyl), —N(ethyl)$_2$, —NH(propyl), —NH(benzyl) or R2 is —NRxRw wherein Rx and Rw are taken together with the nitrogen atom to which they are attached to form a piperazinyl, morpholinyl or piperidinyl.

In one embodiment, each Ra is independently H, methyl, ethyl, n-propyl, isopropyl, n-butyl, sec-butyl, ter-butyl, trifluoromethyl, trifluoromethoxy, methoxy, cyclopropyl, cyclobutyl, cyclopentyl cyclohexyl, heteroaryl of 5-6 members comprising at least one heteroatom selected from oxygen (O), and nitrogen (N); or fluoride atom; Rb is H; Rc is H; R1 is straight or branched alkyl of 3 to 6 carbon atoms, cycloalkyl of 6 or 7 carbon atoms, aryl of 6 carbon atoms, heterocycle of 5 or 6 members or heteroaryl of 5 or 6 members; R2 is H, Cl, methyl, —NH(Me), —N(Me)$_2$, —NH(ethyl), —N(ethyl)$_2$, —NH(propyl), —NH(benzyl) or R2 is —NRxRw wherein Rx and Rw are taken together with the nitrogen atom to which they are attached to form a piperazinyl, morpholinyl or piperidinyl.

In one embodiment, each Ra is independently H, methyl, ethyl, n-propyl, isopropyl, n-butyl, sec-butyl, ter-butyl, trifluoromethyl, trifluoromethoxy, methoxy, or fluoride atom; Rb is H; Rc is H; R1 is an optionally substituted selenium-containing heterocycle, a bridged bicycloalkyl, cycloalkyl or heterocycle; R2 is H.

In one embodiment, each Ra is independently H, methyl, ethyl, n-propyl, isopropyl, n-butyl, sec-butyl, ter-butyl, trifluoromethyl, trifluoromethoxy, methoxy, or fluoride atom; Rb is H; Rc is H; R1 is an optionally substituted selenium-containing heterocycle of 5 or 6 members; R2 is H.

In one embodiment, each Ra is independently H, methyl, ethyl, n-propyl, isopropyl, n-butyl, sec-butyl, ter-butyl, trifluoromethyl, trifluoromethoxy, methoxy, or fluoride atom; Rb is H; Rc is H; R1 is an optionally substituted bridged bicycloalkyl of 7 or 8 carbon atoms; R2 is H.

In one embodiment, each Ra is independently H, methyl, ethyl, n-propyl, isopropyl, n-butyl, sec-butyl, ter-butyl, trifluoromethyl, trifluoromethoxy, methoxy, or fluoride atom; Rb is H; Rc is H; R1 is an optionally substituted bicyclo[2,2,1] heptyl or bicyclo[3,1,1] heptyl; R2 is H.

In one embodiment, each Ra is independently H, methyl, ethyl, n-propyl, isopropyl, n-butyl, sec-butyl, ter-butyl, trifluoromethyl, trifluoromethoxy, methoxy, or fluoride atom; Rb is H; Rc is H; R1 is a 5 or 6 membered selenium-containing heterocycle; R2 is H.

In one embodiment, each Ra is independently H, methyl, ethyl, n-propyl, isopropyl, n-butyl, sec-butyl, ter-butyl, trifluoromethyl, trifluoromethoxy, methoxy, or fluoride atom; Rb is H; Rc is H; R1 is cycloalkyl or heterocycle; R2 is H.

In one embodiment, each Ra is independently H, methyl, ethyl, n-propyl, isopropyl, n-butyl, sec-butyl, ter-butyl, trifluoromethyl, trifluoromethoxy, methoxy, or fluoride atom; Rb is H; Rc is H; R1 is an optionally substituted selenium-containing heterocycle of 5 or 6 or 7 members, an optionally substituted bridged bicycloalkyl of 7 members, an optionally substituted cycloalkyl of 6 or 7 carbon atoms or heterocycle of 5 or 6 members; R2 is H.

In one embodiment, each Ra is independently H, methyl, ethyl, n-propyl, isopropyl, n-butyl, sec-butyl, ter-butyl, trifluoromethyl, trifluoromethoxy, methoxy, or fluoride atom; Rb is H; Rc is H; R1 is cycloalkyl of 6 or 7 carbon atoms or heterocycle of 5 or 6 members; R2 is H.

In one embodiment, each Ra is independently H, methyl, ethyl, n-propyl, isopropyl, n-butyl, sec-butyl, ter-butyl, trifluoromethyl, trifluoromethoxy, methoxy, or fluoride atom; Rb is H; Rc is H; R1 is straight or branched alkyl, cycloalkyl, aryl, heterocycle or heteroaryl; R2 is H.

In one embodiment, each Ra is independently H, methyl, ethyl, n-propyl, isopropyl, n-butyl, sec-butyl, ter-butyl, trifluoromethyl, trifluoromethoxy, methoxy, or fluoride atom; Rb is H; Rc is H; R1 is an optionally substituted 5 or 6 or 7 membered selenium-containing heterocycle, an optionally substituted bridged bicycloalkyl, said bicycloalkyl is a bicyclo[2,2,1] heptyl or bicyclo[3,1,1] heptyl, an optionally substituted straight or branched alkyl of 3 to 10 carbon atoms, an optionally substituted cycloalkyl of 3 to 7 carbon atoms, an optionally substituted aryl of 6 to 10 carbon atoms, an optionally substituted heterocycle of 5-10 members or an optionally substituted heteroaryl of 6-10 members; R2 is H.

In one embodiment, each Ra is independently H, methyl, ethyl, n-propyl, isopropyl, n-butyl, sec-butyl, ter-butyl, trifluoromethyl, trifluoromethoxy, methoxy, or fluoride atom; Rb is H; Rc is H; R1 is an optionally substituted 5 or 6 membered selenium-containing heterocycle, an optionally substituted bridged bicycloalkyl, said bicycloalkyl is a bicyclo[2,2,1] heptyl or bicyclo[3,1,1] heptyl, an optionally substituted cycloalkyl of 5 to 6 carbon atoms, and R2 is H.

In one embodiment, each Ra is independently H, methyl, ethyl, n-propyl, isopropyl, n-butyl, sec-butyl, ter-butyl, trifluoromethyl, trifluoromethoxy, methoxy, or fluoride atom; Rb is H; Rc is H; R1 is straight or branched alkyl of 3 to 10 carbon atoms, cycloalkyl of 3 to 7 carbon atoms, aryl of 6 to 10 carbon atoms, heterocycle of 5-10 members or heteroaryl of 6-10 members; R2 is H.

In one embodiment, each Ra is H; Rb is H; Rc is H; R1 is an optionally substituted cycloalkyl of 3 to 7 carbon atoms; R2 is H.

In one embodiment, each Ra is H; Rb is H; Rc is H; R1 is an optionally substituted 5 or 6 membered selenium-containing heterocycle; R2 is H.

In one embodiment, each Ra is H; Rb is H; Rc is H; R1 is an optionally substituted bicyclo[2,2,1] heptyl or bicyclo[3,1,1] heptyl; R2 is H.

In one embodiment, exemplary compounds of the disclosure include:

Compound 1 (SLLN06)

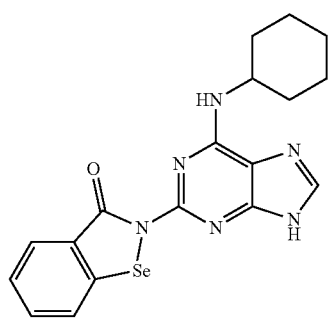 [SMILES: O=c1c2ccccc2[se]n1-c1nc(NC2CCCCC2)c2nc[nH]c2n1]

Compound 2 (SLLN07)

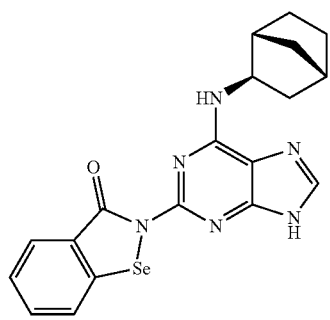

Compound 3 (SLLN08)

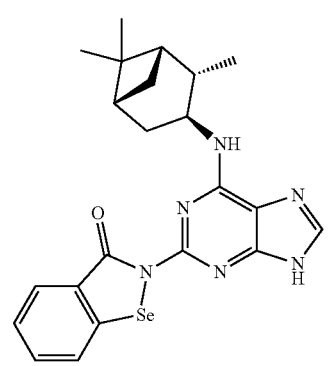

Compound 4 (SLLN11)

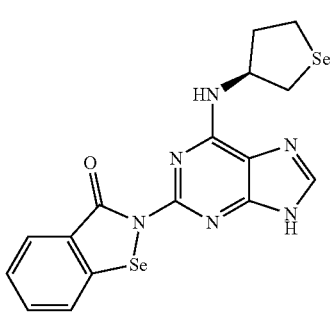

-continued

Compound 5 (SLLN12)

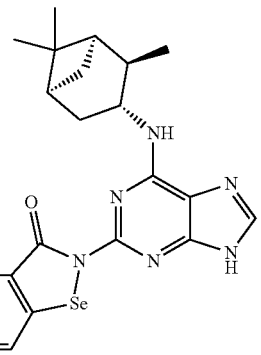

Compound 6 (SLLN13)

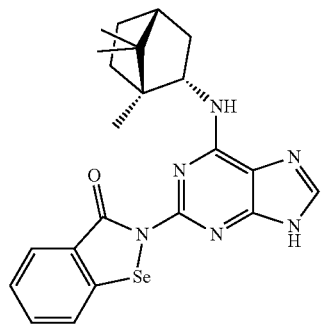

The following is a comparative example compound used as control in certain assays of the disclosure:

Compound 6C (SLLN6C)

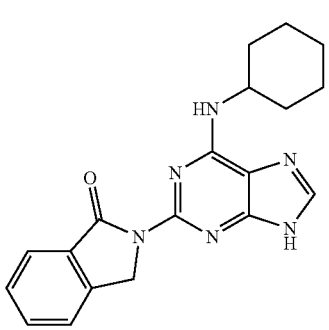

Comparative example:

The term "alkyl", as used herein, is understood as referring to a saturated, monovalent unbranched or branched hydrocarbon chain. Examples of alkyl groups include, but are not limited to, C1-10 alkyl groups, provided that branched alkyls comprise at least 3 carbon atoms, such as C3-10. Lower straight alkyl may have 1 to 6 or preferably 1 to 3 carbon atoms; whereas branched lower alkyl comprise C3-6. Examples of alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, nonyl and decyl. The term "alkyl" is also meant to include alkyls in which one or more hydrogen atom is replaced by a halogen, ie. an haloalkyl including fluoroalkyls of all alkyls defined above: straight or branched fluoroalkyls and straight or branched lower fluoroalkyls, such as trifluoromethyl, difluoromethyl, fluoromethyl, trichloromethyl, dichloromethyl, chloromethyl, trifluoroethyl, difluoroethyl, fluoroethyl.

The terms "alkoxy," represent an alkyl, alkenyl or alkynyl moiety, respectively, which is covalently bonded to the adjacent atom through an oxygen atom.

The term "aryl" represents carbocyclic moiety containing at least one benzenoid-type ring (i.e., may be monocyclic or polycyclic). Examples include but are not limited to phenyl, tolyl, dimethylphenyl, aminophenyl, anilinyl, naphthyl, anthryl, phenanthryl or biphenyl. Preferably, the aryl comprises 6 to 10 or more preferably 6 carbon atoms.

The term "cycloalkyl" represents optionally substituted cyclic hydrocarbon moiety having 3 to 10 carbon atoms. Examples of "cycloalkyl" groups include but are not limited to cyclopropyl, cyclobutyl, cyclopentyl, and cyclohexyl. Lower cycloalkyls comprise 3 to 6, or alternatively any of 3, 4, 5 or 6 carbon atoms. This term includes without limitation, for example, cyclopropyl, cyclobutyl, cyclopentyl and cyclohexyl.

The term "heteroaryl" represents a 5 to 11 membered aromatic cyclic moiety wherein said cyclic moiety is comprising at least one heteroatom selected from oxygen (O), sulfur (S) or nitrogen (N). Heteroaryls may be monocyclic or polycyclic rings. Heteroaryls may be 5 to 6 membered monocyclic ring or 5 membered monocyclic ring or 6 membered monocyclic ring. membered monocyclic ring may be 7 to 12 membered bicyclic ring or 9 to 10 membered bicyclic ring. When heteroaryl is a polycyclic ring, the rings comprise at least one ring comprising the heteroatom and the other rings may be cycloalkyl, aryl or heterocycle and the point of attachment may be on any available atom. This term includes without limitation, for example, furyl, thienyl, pyrrolyl, imidazolyl, oxazolyl, thiazolyl, triazolyl, tetrazolyl, pyridyl, pyrazinyl, pyrimidinyl, pyridazinyl, quinolinyl, isoquinolinyl, indolyl.

The term "heterocycle" represents a 3 to 11 membered saturated, partially saturated (i.e. comprising one or more double bonds provided that it is not aromatic) cyclic moiety wherein said cyclic moiety is comprising at least one heteroatom selected from oxygen (O), sulfur (S) or nitrogen (N). Heterocycles may be monocyclic or polycyclic rings. Heterocycles may be 3 to 6 membered monocyclic ring or 5 to 6 membered monocyclic ring. When heterocycle is a polycyclic ring, the rings comprise at least one ring comprising the heteroatom and the other rings may be cycloalkyl, aryl or heterocycle and the point of attachment may be on any available atom. This term includes without limitation, for example, aziridinyl, oxiranyl, thiiranyl, azirinyl, oxirenyl, thiirenyl, azetidinyl, oxetanyl, oxetyl, pyrrolidinyl, oxolanyl, thiolanyl, piperidinyl, oxanyl, thianyl, azepanyl, oxepanyl, morpholinyl, piperazinyl, homopiperazinyl.

The term "selenium-containing heterocycle" represents a 3 to 10 membered saturated cyclic moiety wherein said cyclic moiety is comprising at least one selenium (Se), preferably one Se, atom in cyclic ring. Heterocycles may be monocyclic or polycyclic rings. Heterocycles may be 3 to 7 membered monocyclic ring, preferably 5 to 6 membered monocyclic ring.

As used herein, the expression "alkyl", "alkoxy", "aryl", "cycloalkyl", "heteroaryl", "heterocycle", "alkoxy," "alkenyloxy," "alkynyloxy", selenium-containing heterocycle and bridged bicycloalkyl, bicyclo[3,1,1] heptyl or bicyclo[2,2,1] heptyl (including lower alkyl and lower cycloalkyl) are all independently optionally substituted by one or more substituents.

In another embodiment, the term "optionally substituted", "optionally substituent" or "substituent" preferably represents halogen, C1-6alkyl, C2-6alkenyl, C2-6alkynyl, C1-6 alkoxy, C2-6alkenyloxy, C2-6alkynyloxy, —NR40R41, —C(O)NR40R41, —NR40COR41, carboxy, azido, cyano, hydroxyl, nitro, nitroso, —OR40, —SR40, —S(O)$_{0-2}$R40, —C(O)R40, —C(O)OR40 and —SO2NR40R41; wherein R40 and R41 are each independently H, C1-6alkyl, C2-6alkenyl or C2-6alkynyl. In still another embodiment, the term "optionally substituted", "optionally substituent" or "substituent" preferably represents halogen, C1-6alkyl, C2-6alkenyl, C1-6 alkoxy, —NR40R41, —C(O)NR40R41, —NR40COR41, carboxy, hydroxyl, nitro, —SR40, —S(O)$_{0-2}$R40, —C(O)R40, —C(O)OR40 and —SO$_2$NR40R41; wherein R40 and R41 are each independently H, or C1-6alkyl.

The term "independently" means that a substituent can be the same or a different definition for each item.

The compounds as defined herein may include a chiral center which gives rise to enantiomers. The compounds may thus exist in the form of two different optical isomers, that is (+) or (−) enantiomers. All such enantiomers and mixtures thereof, including racemic or other ratio mixtures of individual enantiomers, are included within the scope of the invention. The single enantiomer can be obtained by methods well known to those of ordinary skill in the art, such as chiral HPLC, enzymatic resolution and chiral auxiliary derivatization.

It will also be appreciated that the compounds in accordance with the present disclosure can contain more than one chiral centre. The compounds of the present invention may thus exist in the form of different diastereomers. All such diastereomers and mixtures thereof are included within the scope of the invention. The single diastereomer can be obtained by methods well known in the art, such as HPLC, crystalisation and chromatography.

There is also provided pharmaceutically acceptable salts of the compounds of the present disclosure. What is meant by the term pharmaceutically acceptable salts of the compounds is that they are derived from pharmaceutically acceptable inorganic and organic acids and bases.

For example, conventional non-toxic salts include those derived from inorganic acids such as hydrochloric, hydrobromic, sulfuric, sulfamic, phosphoric, nitric, perchloric and the like, as well as salts prepared from organic acids such as formic, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, benzenesulphonic, naphthalene 2 sulphonic, ethane disulfonic, oxalic, isethionic, trifluoroacetic and the like.

Other acids, while not in themselves pharmaceutically acceptable, may be useful as intermediates in obtaining the compounds of the disclosure and their pharmaceutically acceptable acid addition salts. Salts derived from appropriate bases include alkali metal, alkaline earth metal or ammonium salts. The salt(s) must be "acceptable" in the sense of not being deleterious to the recipient thereof.

The pharmaceutically acceptable salts of the compounds of this disclosure can be synthesized from the compounds of this disclosure which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

The term "solvate" means that a compound as defined herein incorporates one or more pharmaceutically acceptable solvents including water to give rise to hydrates. The solvate may contain one or more molecules of solvent per molecule of compound or may contain one or more molecules of compound per molecule of solvent. Illustrative non-limiting examples of hydrates include monohydrate, dihydrate, trihydrate and tetrahydrate or semi-hydrate. In one embodiment, the solvent may be held in the crystal in various ways and thus, the solvent molecule may occupy lattice positions in the crystal, or they may form bonds with salts of the compounds as described herein. The solvate(s) must be "acceptable" in the sense of not being deleterious to the recipient thereof. The solvation may be assessed by methods known in the art such as Loss on Drying techniques (LOD).

It will be appreciated by those skilled in the art that the compounds in accordance with the present disclosure can exist in several different crystalline forms due to a different arrangement of molecules in the crystal lattice. This may include solvate or hydrate (also known as pseudopolymorphs) and amorphous forms. All such crystalline forms and polymorphs are included within the scope of the disclosure. The polymorphs may be characterized by methods well known in the art. Examples of analytical procedures that may be used to determine whether polymorphism occurs include: melting point (including hot-stage microscopy), infrared (not in solution), X-ray powder diffraction, thermal analysis methods (e.g. differential scanning calorimetry (DSC) differential thermal analysis (DTA), thermogravimetric analysis (TGA)), Raman spectroscopy, comparative intrinsic dissolution rate, scanning electron microscopy (SEM).

When there is a sulfur atom present, the sulfur atom can be at different oxidation levels, ie. S, SO, or $SO_2$. All such oxidation levels are within the scope of the present disclosure. When there is a nitrogen atom present, the nitrogen atom can be at different oxidation levels, ie. N or NO. All such oxidation levels are within the scope of the present disclosure.

As defined herein "subject" refers to both human and non-human subjects. Preferably the subject is human.

Without being bound to theory, it is believed that the ability of the synthesized compounds to inhibit multiple key targets involved in CSC and metastasis signaling may provide a significant potential for the management of cancer, in particular metastatic cancers.

As used herein, "treatment" or "treating" refers to at least i) controlling or ameliorating at least one disease described herein, at least for the duration of said treatment. Advantageously, the treatment could i) reduce the occurrences of a further episode, or ii) reduce its severity or iii) prevent occurrences of further episodes, at least for the duration of the therapy. Although not limited to such patients, is expected to be particularly useful to the treatment of patients who have suffered a previous episode associated with diseases described herein, or are otherwise considered to be at increased risk of said diseases.

The expression "cancer" includes, but is not limited to carcinomas, sarcomas, melanomas; lymphoma, leukemia and myelomas; blastomas; germ cell tumor; glioma and other CNS cancers.

In one embodiment, the carcinoma is a cancer of the bladder, breast, cervix, colon, esophagus, kidney, liver, larynx, lung (small and non-small cell lung cancer), oral cavity, ovary, pancreas, pleura, prostate, skin (basal and squamous), stomach, thyroid or uterus.

In one embodiment, the sarcoma is osteosarcoma, chondrosarcoma, liposarcoma, neurosarcoma, rhabdomyosarcoma, Erwing sarcoma or fibrosarcoma.

In one embodiment, the melanoma is malignant melanoma, lentigo maligna melanoma, superficial spreading melanoma, acral lentiginous melanoma, mucosal melanoma, nodular melanoma, polypoid melanoma, desmoplastic melanoma, amelanotic melanoma or soft-tissue melanoma.

In one embodiment, the lymphoma, leukemia and myelomas is acute lymphocytic leukemia, B-cell lymphoma, Burketts lymphoma, Hodgkin and Non-Hodgkin lymphoma, acute and chronic myelogenous leukemias, promyelocytic leukemia or multiple myeloma.

In one embodiment, the blastoma is a blastoma derived from immature "precursor" cells or embryonic tissue, neuroblastoma, retinoblastoma, pleuropulmonary blastoma, nephroblastoma (Wilms tumor) or hepatoblastoma.

In one embodiment, the germ cell tumor is a seminoma, dysgerminoma or teratocarcinoma tumor.

In one embodiment, the glioma and other CNS cancers are ependymomas, astrocytomas, oligodendrogliomas, glioblastomas or oligoastrocytomas.

In one embodiment, the cancer is a breast, prostate or pancreatic cancer. In a further embodiment, the cancer is Metastatic cancer. In one embodiment, the metastatic cells are cells enriched in CSC markers. In a further embodiment, the inhibition of metastasis is in vitro or in vivo. In a further embodiment, the cancer is a refractory cancer. In still a further embodiment, the cancer is metastatic triple negative breast cancer, Her2, luminal, basal-like, inflammatory breast cancer or both refractory and metastatic Her2+ breast cancer.

In another embodiment, the present disclosure provides a combination comprising a therapeutically effective amount of a compound, as defined herein, and a therapeutically effective amount of at least one or more therapeutic agents useful in the method of the present disclosure selected from: Alkylating agents, Anti-metabolites, Plant alkaloids and terpenoids, *Vinca* alkaloids, Podophyllotoxin, Taxanes, Topoisomerase inhibitors, and Cytotoxic antibiotics.

In another embodiment, the present invention provides a combination comprising a therapeutically effective amount of a compound, as defined herein, and a therapeutically effective amount of at least one or more therapeutic agents useful in the method of the present disclosure including but not limited to imatinib, paclitaxel, docetaxel, cisplatin, doxorubicine, vinblastine, zoledronate and/or in conjunction with antimetastatic agents, antiangionevic agents such as avastatin, and targeted therapeutics including EGFR, VEGFR, WNT, Aurora, etc. and antiapoptotic compounds such as Velcade™, agents targeting synthesis of estrogens or estrogen signaling through estrogen receptors including but not limited to arimidex and tamoxifen, agents targeting biosynthesis of androgens or androgen signaling through the androgen receptor including but not limited to bicalutamide, agents targeting HER2 including but not limited to trastuzumab, agents targeting BRAF including but not limited to Vemurafenib, or agents targeting members of the MAP kinase family or their upstream or downstream effector kinases.

It will be clear to a person of ordinary skill that the amounts and/or ratios of therapeutic agents will be readily adjusted. It will be understood that the scope of combinations described herein is not particularly limited, but includes in principle any therapeutic agent useful for preventing or treating the diseases described herein.

It will also be appreciated that the amounts and/or ratios of therapeutic agents for use in treatment will vary not only with the particular agent selected but also with the route of administration, the nature of the condition for which treatment is required and the age and condition of the patient and will be ultimately at the discretion of the attendant physician.

The compounds defined herein can be administered concurrently to the one or more agents used herein in the methods and combinations. The desired doses may conveniently be presented in a single dose or as divided dose administered at appropriate intervals, for example as two, three, four or more doses per day or continuously such as in a perfusion. The compound can be administered on a dosage regimen distinct to the one or more agents used herein in the methods and combinations. Alternatively, the compound can be administered sequentially or concurrently in distinct formulations or in a common formulation.

Pharmaceutical compositions may comprise pharmaceutically acceptable carrier(s) and/or excipient(s). Many pharmaceutically acceptable carrier(s) and/or excipient(s) are known in the art. It will be understood by those in the art that a pharmaceutically acceptable carrier must be compatible with the other ingredients of the formulation and tolerated by a subject in need thereof. or liquid preparations, such as oral or sterile parenteral solutions or suspensions. The proportion of each carrier is determined by the solubility and chemical nature of the agent(s), the route of administration, and standard pharmaceutical practice.

In order to ensure consistency of administration, in an embodiment of the present invention, the pharmaceutical composition is in the form of a discrete dosage units and may be prepared by any of the methods well known in the art of pharmacy. All methods include the step of bringing into association the active compound with a liquid carrier or solid carrier or both and then, if necessary, shaping the product into the desired formulation.

Pharmaceutical compositions suitable for oral administration may conveniently be presented as discrete units such as capsules, cachets or tablets each containing a predetermined amount of the active ingredient; as a powder or granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds and combinations according to the invention may also be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

The following examples are provided to further illustrate details for the preparation and use of the compounds of the present invention. They are not intended to be limitations on the scope of the instant invention in any way, and they should not be so construed. Furthermore, the compounds described in the following examples are not to be construed as forming the only genus that is considered as the invention, and any combination of the compounds or their moieties may itself form a genus.

Examples: Chemistry—Preparation of the Compounds of the Invention

Compounds of the present disclosure can be prepared according to the procedures denoted in the following reaction Scheme 1 and examples or modifications thereof using readily available starting materials, reagents, and conventional procedures or variations thereof well-known to a practitioner of ordinary skill in the art of synthetic organic chemistry. Specific definitions of variables in the Schemes are given for illustrative purposes only and are not intended to limit the procedures described.

Scheme 1: General synthesis of the compounds disclosed herein.

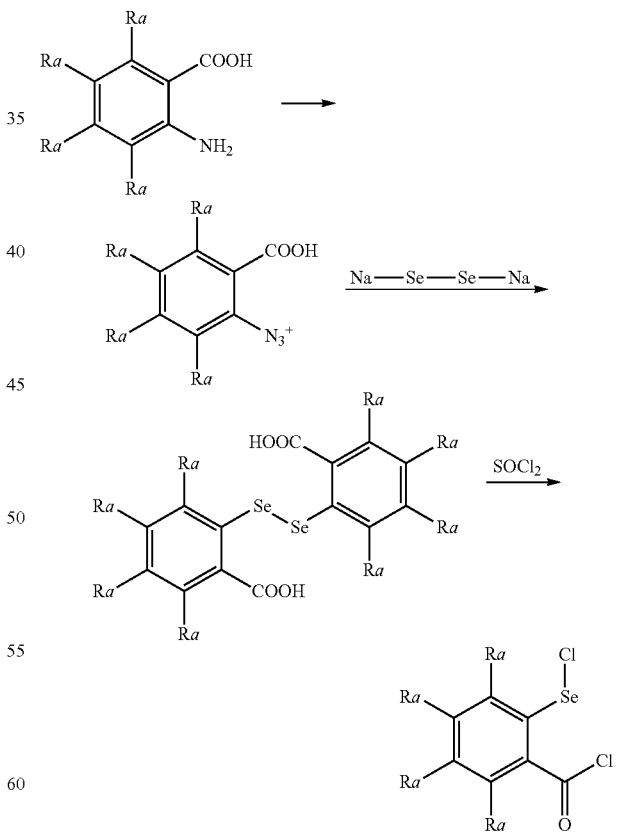

A 2-amino benzoic acid compound is converted to the corresponding diazonium salt (e.g. by treatment with HCl followed by a nitrite salt such as sodium nitrite). The diazonium salt is then reacted with Na—Se—Se—Na, prepared in accordance with known procedures, to prepare the 2,2′-diselanediyldibenzoic acid compound which is optionally purified. The latter compound is then reacted with thionyl chloride to provide the required benzoyl chloride reagent.

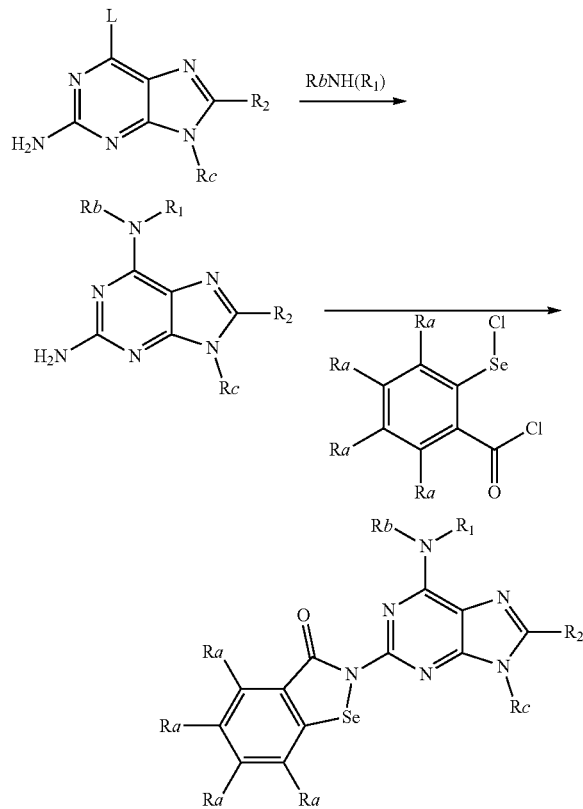

A 2-aminopurine having a suitable leaving group L at position 6 is reacted with amine RbNH(R₁) to yield the corresponding 2,6-diamino-purine intermediate. The latter intermediate is reacted with the benzoyl chloride reagent prepared above to provide the desired compound in accordance with the present disclosure.

Example 1: Synthesis of

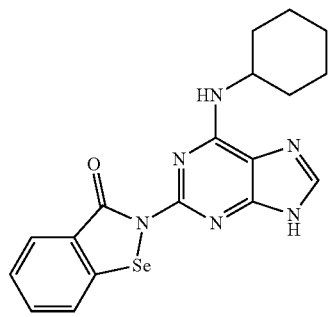

Step 1:

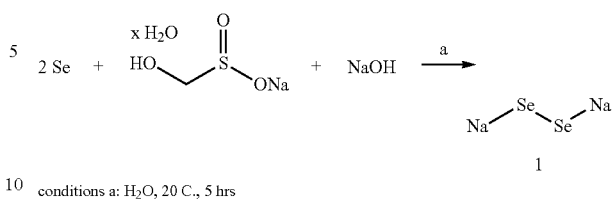

conditions a: H₂O, 20 C., 5 hrs

Sodium hydroxide (1.46 g, 36.5 mmole, Sigma-Aldrich 221465) was dissolved in water (30 mL) in a 250 mL RB flask. Sodium hydroxymethanesulfinate hydrate (2.5 g, approximately 21.2 mmole, Sigma-Aldrich 71530) was added and dissolved upon sonication and stirring at 20 C (room temp.). Selenium powder (2.9 g, 36.7 mmole, Sigma-Aldrich 209651) then was added and the mixture was vigorously stirred by magnetic stir-bar at room temperature for 5 hrs. All of the solids dissolved resulting in a dark-red aqueous solution of disodium diselenide 1.

Step 2:

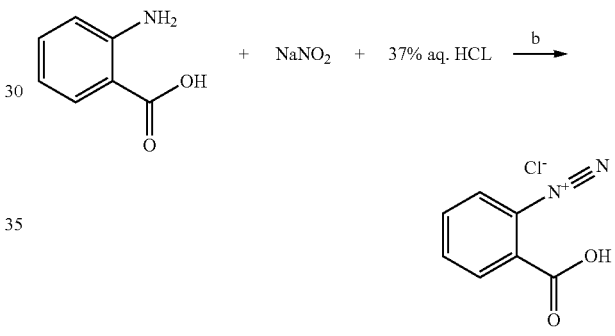

conditions b: H₂O, -10 C., 1 hr

Anthranilic acid (5 g, 36.4 mmole, Sigma-Aldrich A89855) suspension in water (30 mL) was vigorously stirred by magnetic stir-bar in a 250 mL RB flask. Concentrated hydrochloric acid (37%, 7.5 mL, 90 mmole, Sigma-Aldrich 258148) was added to result in thicker suspension of anthranilic acid hydrochloride (stirring was difficult but possible). The suspension was then cooled to -10 C (dry ice/acetone bath). Sodium nitrite (2.52 g, 36.5 mmole, Sigma-Aldrich 237213) was dissolved in water (15 mL) and this solution was added dropwise in 10 min. into the vigorously stirred suspension of anthranilic acid chlorohydrate at -10 C. Addition of every drop resulted in formation of orange-red colour and slow dissolution of the suspension. After the addition was accomplished, the mixture continued to stir for additional 1 hour at -10 C, resulting in a clear, orange-red solution of the diazonium salt 2.

Step 3:

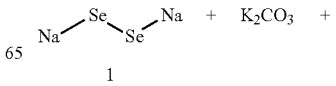

-continued

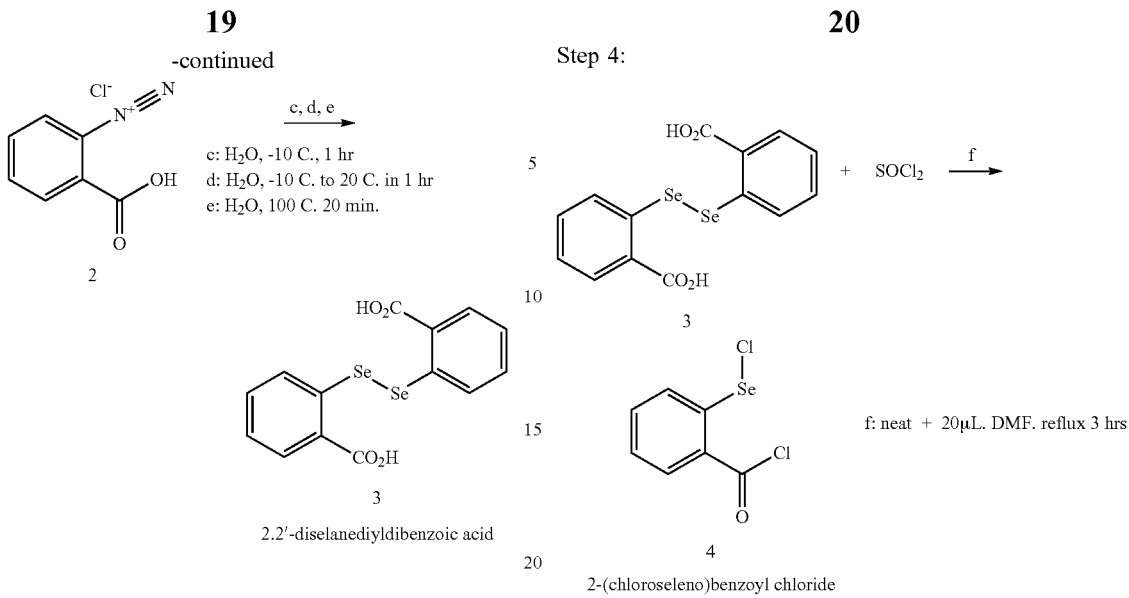

2.2'-diselanediyldibenzoic acid

Potassium carbonate (5.04 g, 36.5 mmole, Sigma-Aldrich 60109) was added to the aqueous solution 1 and was dissolved. The mixture was stirred vigorously and was cooled to 0 C. Then, the aqueous diazonium salt solution 2 at −10 C was added in small portions in approximately 30 min. The dark-red mixture containing some suspension continued to stir at −10 C for 1 hour, then it was allowed to warm up to 20 C in 1 hour, followed by stirring at 100 C (oil bath) for 20 min. The mixture became clear brown-red solution with some black precipitate formed (presumably selenium powder). pH of this mixture was 7.59 (measured by pH electrode meter). The mixture was then filtered by suction via a 45 mm filter membrane (about 1.5 g of black solid was separated).

Concentrated hydrochloric acid (37%, 20 mL, 240 mmole, Sigma-Aldrich 258148) was added to the above clear filtrate resulting in formation of red precipitate (pH of this mixture was about 0). The mixture was filtered by suction via a 45 mm filter membrane. the separated red solid was rinsed with water (4×20 mL). The solid was purified by dissolving in aqueous sodium hydroxide solution (1.6 g NaOH, 40 mmole in 25 mL water) giving a clear, red solution, pH=12.7. Concentrated hydrochloric acid (37%, 5 mL, 60 mmole, Sigma-Aldrich 258148) was added, the resulting red suspension was vigorously shaken (pH=0.35), was filtered by suction via a 45 mm filter membrane. The separated brown solid was rinsed with water (4×20 mL) and was dried for 16 hrs in vacuo in a dessicator containing solid sodium hydroxide pellets, to give: 4.27 g brown solid, yield from anthranilic acid: 60%. Analytical HPLC (same conditions as described previously in the protocol for the synthesis of DW-2) indicated presence of a mayor peak product at 9.1 min. 61% (220 nm), 69% (254 nm) content by UV absorption. The above crude product was then further purified by crystallization from anhydrous ethanol to give: 1.67 g of light-brown solid, Anal. HPLC: at 9.1 min. 98% (220 nm), 97% (254 nm) content. The expected structure of 2,2'-diselanediyldibenzoic acid 3 was confirmed by LC-MS and by 1HNMR (dmso-d6). Final yield from anthranilic acid: 23%

Step 4:

2-(chloroseleno)benzoyl chloride

The compound 3 (2,2'-diselanediyldibenzoic acid, 1.67 g, 4.17 mmole) was stirred in neat thionyl chloride (15 mL, Fluka 8852). Catalytical amount of anhydrous DMF (20 mL) was added. The clear solution was stirred for 3 hrs. at 80 C under a reflux condenser, fitted on top with a calcium chloride drying tube. The reaction mixture was then concentrated in vacuo (rotary evaporator) and thionylm chloride residues were removed by re-concentration with dichloromethane. The final crude product was purified by dissolving in hexane, filtration and concentration of the clear hexane solution in vacuo to give 4: 1.77 g yellow, crystalline solid (yield: 84%). Stored in closed vial at −5 C.

Step 5:

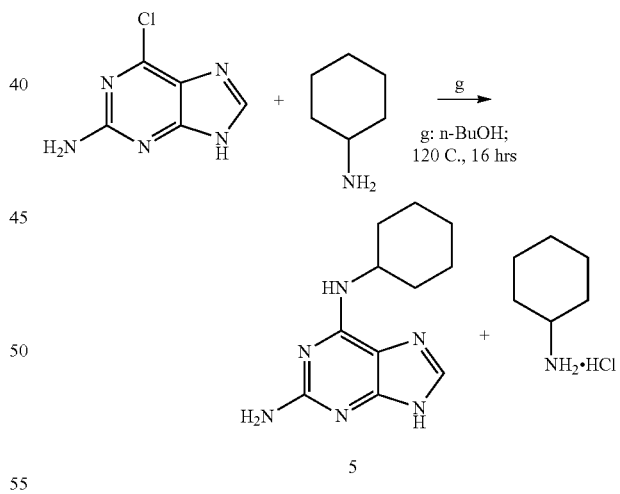

A mixture of 2-amino-6-chloropurine (100 mg, 0.59 mmole, Oakwood Chemical 010750) and cyclohexylamine (270 mL, 2.36 mmole, Sigma-Aldrich 240648) was stirred in n-butanol (3 mL) in a 8 mL capped glass vial at 120 C (oil bath) for 16 hrs. All solids dissolved giving a colourless solution. Work up: RM was concentrated in vacuo on rotary evaporator at 90 C (water bath). The colourless oily residuo was re-concentrated with 2×15 mL EtOH, then with 2×15 mL EtOAc, then with 2×15 mL diethyl ether to give semi-solid white foam. This residuo was then dried in high vacuo to give 228 mg mg of beige solid. This crude product was purified via flash column chromatography (50 g silica gel, eluted with 1% to 4% MeOH/DCM). Fractions of 25 mL were collected, analized by TLC (10% MeOH/DCM), combined (about 700 mL), concentrated in vacuo, residuo transferred into a 100 mL RB flask, re-concentrated with EtOAc, then with diethyl ether, dried in vacuo to give: N6-cyclohexyl-9H-purine-2,6-diamine 5 as 128 mg off-white solid. Analytical HPLC: single peak at 8.6 min. 100% (220 nm), 100% (254 nm)

Conditions #2 for HPLC: analytical column "LiChrosorb" Reverse Phase silica gel, 5 mm C8 endcapped, 250 mm×4.6 mm eluent A=0.1% TFA/water; eluent B=0.1% TFA in acetonitrile, gradient: from 5% B to 100% B in 15 min.; flow=1 mL/min. Note: it is of importance to remove the cyclohexylamine hydrochloride (by the flash chromatography as described above), since it can react in the next, final synthetic step.
Step 6

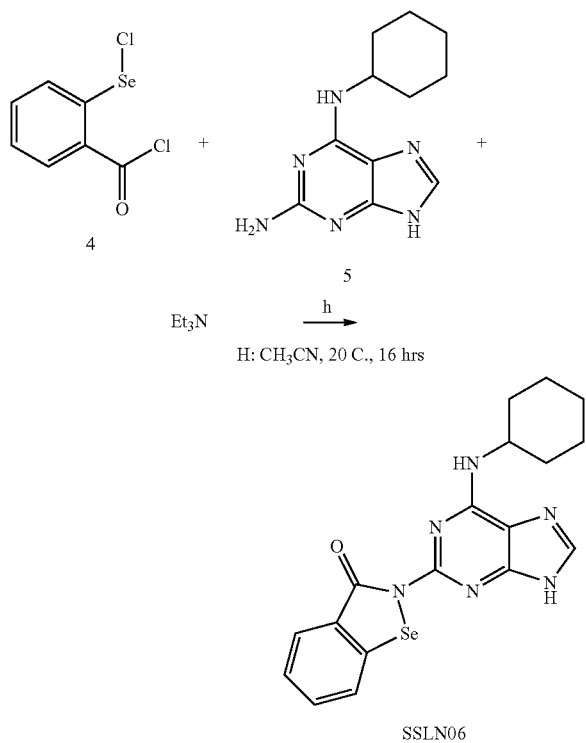

5 (50 mg, 0.21 mmole) was dissolved on heating in acetonitrile (2 mL) in a 8 mL glass vial containing a magnetic stir-bar. This solution was then cooled down to 20 C (RT). No precipitation was observed. Triethylamine (60 mL, 0.43 mmole, Sigma-Aldrich T0886) was added. The mixture was vigorously stirred at RT and a solution of 4 (55 mg, 0.22 mmole) in acetonitrile (1 mL) was added. Reaction mixture was stirred at RT for 16 hrs. resulting in formation of yellow suspension of the product. Filtration by suction via a 45 mm filter membrane, rinsing with ice-cold acetonitrile (1 mL), drying in vacuo gave 56 mg of yellow solid (yield: 63%). Analytical HPLC (conditions #2) of the isolated solid indicated presence of mayor peak product at 11.9 min, 80% (220 nm), 77% (254 nm). Analytical HPLC (conditions #2) of the yellow filtrate indicated presence of mostly starting material 5 at 8.6 min, 65% (220 nm), 70% (254 nm).

The crude product was purified by flash column chromatography on 5 g silica gel, eluted with a stepwise gradient from 2% to 5% MeOH in chloroform. The collected fractions were analized by TLC (10% MeOH/CHCl3) and by analytical HPLC. The chosen fractions were combined, concentrated in vacuo, the residuo was rinsed with ice-cold ether (1 mL) and was dried in vacuo to give: SLLN06: 26 mg (yield: 29%) off-white solid. Analytical HPLC (conditions #2): peak at 11.3 min. 97% (220 nm), 99% (254 nm). The expected structure was confirmed by LC-MS and 1HNMR (dmso-d6) spectra.

Example 2: Synthesis of

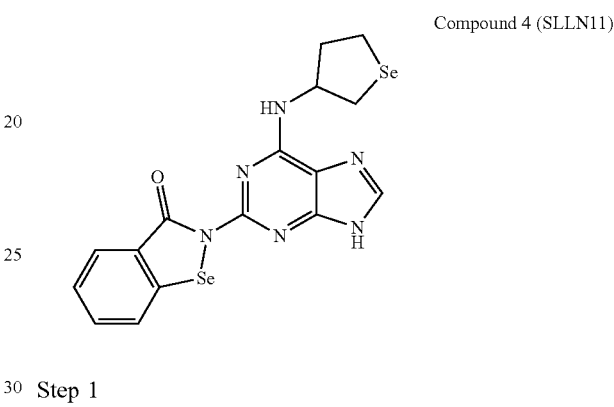

Step 1

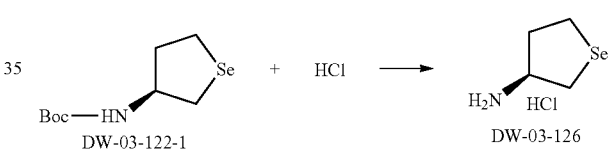

4.8 g (19.12 mmole) of DW-03-122-1 was stirred in about 20 mL of 4M HCl in dioxane in a 250 mL round bottom flask. (commercial Sigma-Aldrich). The pink mixture/suspension was then stirred at 45 C (oil bath) under reflux condenser with CaCl$_2$ drying tube on top for 12 hrs. The reaction mixture was concentrated on rotary evaporator to dryness to give pink solid residuo. About 100 mL diethyl ether was added, the mixture stirred for 30 min. at RT. The suspension was filtered by suction via 45 μm membrane, rinsed with diethyl ether, dried in vacuo to give DW-03-126: 3.53 g slightly pink solid (99% yield).

TLC (EtOAc/hexane 3/7; visualized with iodine vapour): absence of the start. material DW-03-122-1

Step 2

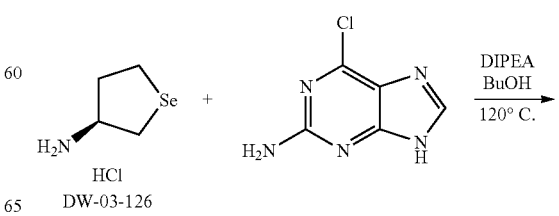

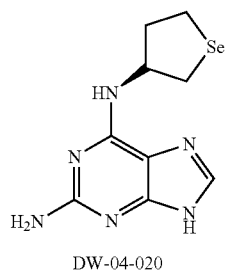

DW-04-020

A mixture of 500 mg of 2-amino-6-chloropurine (CAS 10310-21-1; Oakwood 010750), 665 mg of DW-03-126 and 2 mL (3.8 eq.) diisopropylethylamine (DIPEA) was stirred (magnetic stir bar) in 20 mL of n-butanol in a tightly closed glass reaction tube, flushed with nitrogen before closing. The suspension was stirred at 120 C (oil bath) for 16 hrs (overnight). The next day the reaction mixture was a suspension in brown solution. It was cooled to room temp. and an aliquote was analized by HPLC to assess completion. 165 mg (0.88 mmole, 0.3 eq.) of DW-03-126 (extra St. Mat.) and 0.3 mL DIPEA (1.68 mmole, 0.6 eq.) were added. The reaction mixture was then again stirred at 120 C overnight in the closed vessel.

The mixture was concentrated on rotary evaporator in vacuum at +70 C water bath, re-concentration with ethanol (2x), drying in high vacuo gave 2 g of crude dark brown oil. This material was mixed with about 10-20 mL ethanol which gave a suspension at RT, it was sonicated 2 min. then cooled to 0 C and filtered by suction via 45 μm filter membrane to give brown solid, which was rinsed with 5-10 mL cold ethanol at 0 C, then with diethyl ether and was dried in vacuo to give 643 mg (yield: 77%). The material was used in the next step DW-04-022

Step 3

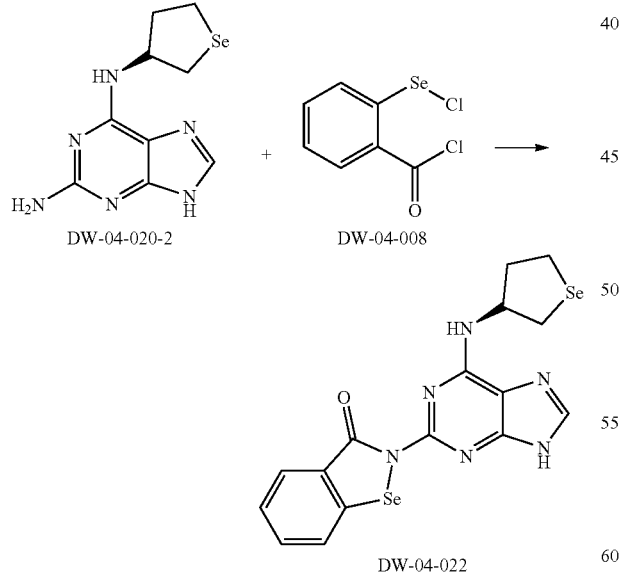

In a 250 mL round bottom flask, 640 mg of DW-04-020-2 was stirred as suspension in 70 mL dichloromethane at room temperature. 1064 μL of diazabicyclo undecane (DBU) was added. All solids slowly dissolved to give yellow/brown clear solution. Then, a solution of 706 mg DW-04-008 in 30 mL dichloromethane was added via syringe in about 2 min. at room temperature. Reaction mixture darkened and remained clear-brown. The round bottom flask was stoppered and the plastic stopper was secured with a plastic clamp. After stirring at room temperature for 10 min. precipitate began slowly forming. Reaction mixture was stirred at room temperature for 15 hrs. A white/beige suspension was formed. HPLC of an aliquote post 15 hrs can be used to assess the progress. Filtration of the reaction mixture by suction via 45 μm membrane, rinse of the solid with DCM (3x about 20 mL), rinse with methanol (2x20 mL) then rinse with ether (3x about 20 mL) and drying in vacuo gave 619 mg slightly yellow solid; yield: 60%

Example 3: Synthesis of

Compound 3 (SLLN08)

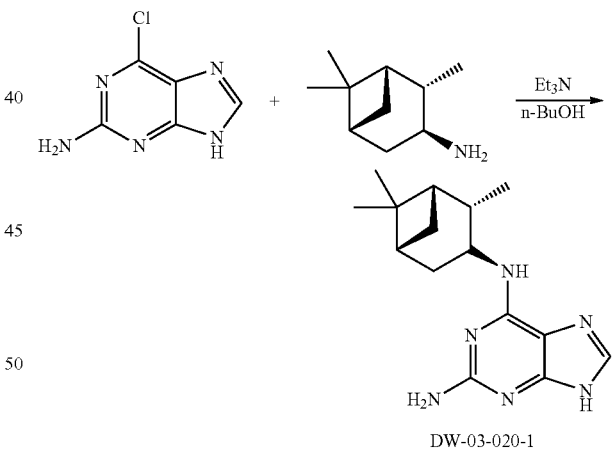

Step 1:

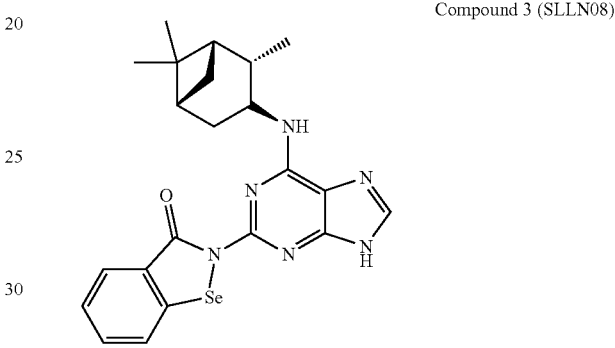

786 mg of (1S,2S,3S,5R)-(+)-Isopinocampheylamine (CAS 13293-47-5 Aldrich 391662-1G), 500 mg of 2-amino-6-chloropurine, 860 uL of triethyl amine were mixed to 3 mL of n-BuOH. Reaction mixture was stirred in a large (30 mL) closed glass pressure tube at 120-125 C (oil bath) for 16 hrs (the area above the reaction mixture was flushed with nitrogen just before closure). Reaction mixture was a suspension at the starting point. Next day it became a clear, brown solution. The Work up consisted of concentration on rotary evaporator in vacuum at +90 C water bath, re-concentration with ethanol (3x), EtOAc (2x), diethyl ether (3x) gave a crude beige solid.

The compound can be purified: via flash column chromatography—50 g silica gel equilibrated with pure dichloromethane, crude product loaded in 2% MeOH/dichloromethane, eluted with 2% to 4% MeOH/DCM.

Fractions of 25 mL each (testubes) were collected, analized by TLC (developed in 10% MeOH/DCM), homogeneity of the main product in chosen fractions was confirmed by analytical HPLC. The chosen fractions were combined (about 3 L), concentrated in vacuo, residuo transferred into a 100 mL RB flask, re-concentrated with EtOAc, then with diethyl ether, then the residuo was dried in vacuo to give a beige solid.

Step 2

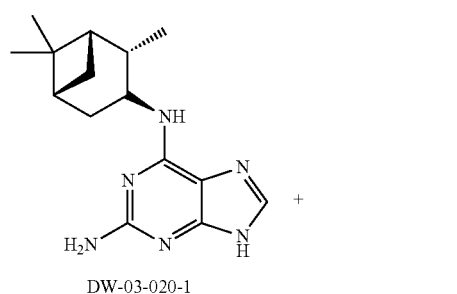

DW-03-020-1

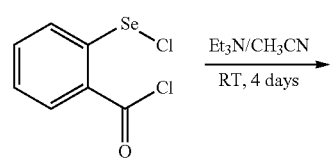

DW-03-026

Similarly to the conditions described above, the desired compound was obtained, except that acetonitrile and trimethylamine were used. 585 mg of the acyl chloride reagent in 15 mL of acetonitrile was added to 585 mg of the amine compound in 25 mL of acetonitrile and the reaction was stirred at room temperature for 4 days. obtained: 53 mg of crude yellow solid was isolated as a precipitate, filtered, rinsed with cold CH3CN, and dried.

MW: 467.43
m/z: 468.12 (100.0%), 466.12 (51.9%).

Example 4 Synthesis of

Compound 2 (SLLN07)

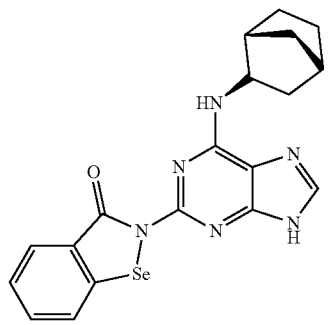

Step 1

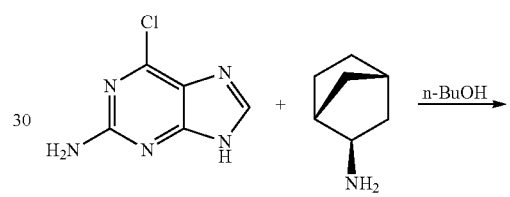

500 mg of 2-amino-6-chloropurine (CAS 10310-21-1; Oakwood 010750) was stirred (magnetic stir bar) in 12 mL of n-butanol in a glass reactor tube. 983 mg of exo-2-aminonorbornane (CAS 7242-92-4; Aldrich 179604) was added in 3 mL n-butanol. Reaction mixture was stirred in closed vial at 120 C (oil bath) for 14 hrs (overnight). The white suspension slowly dissolved. Next day RM was clear, dark brown ("tea") solution. The work up consisted of concentration on rotary evaporator in vacuum at +70 C water bath, re-concentration with ethanol+1 mL Et₃N (to assure complete removal of HCl from the product) (2×), EtOAc (2×), diethyl ether (1×) to give 1168 mg of an orange solid. This material was triturated with diethyl ether to remove most of the coloured impurities; filtration (suction via 45 m membrane filter), drying in vacuo gave 982 mg off-white solid; contains Et₃N and cyclohexylamine HCl salts. The compound can be further purified via flash column chromatography (50 g silica gel with DCM, eluted with 2% to 4% MeOH/DCM), concentrated in vacuo, residuo transferred into a 100 mL RB flask, reconcentrated with EtOAc, then ether, dried in vacuo to give 640 mg of a beige solid.

Step 2:

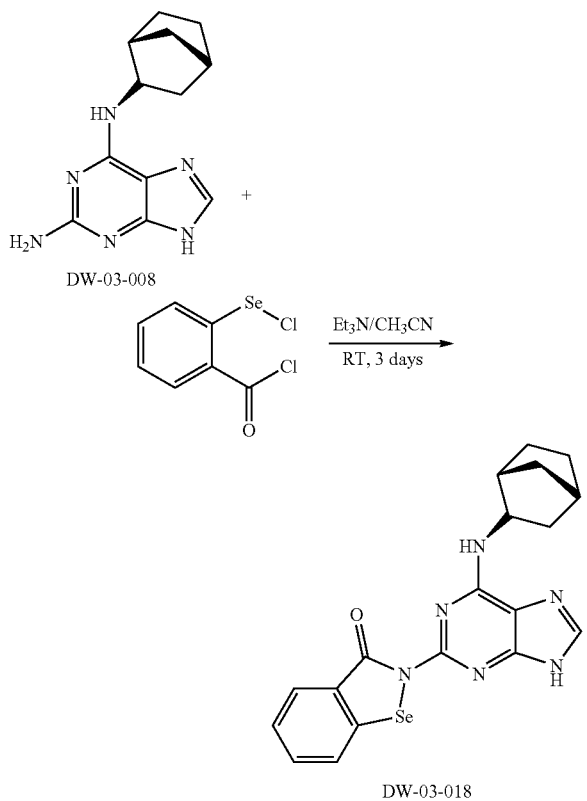

Similarly to the conditions described above, the desired compound was obtained, except that acetonitrile and trimethylamine were used and stirred at room temperature for 3 days. 312 mg of the acyl chloride reagent in 4 mL of acetonitrile was added to 300 mg of the amine compound in 10 mL of acetonitrile and the reaction was stirred at room temperature for 3 days. A crude yellow solid was isolated as a precipitate, filtered, rinsed with cold CH3CN, and dried.
MW: 425.35
m/z: 426.07 (100.0%),
424.07 (48.2%), Examples: Biology The Applicant has surprisingly found molecules able to target cancer stem cell populations in vitro, in addition to inhibiting their proliferation. In vivo preclinical data using established invasive breast cancer models representative of breast cancer subtypes also demonstrated the ability of compound 4 (in the figures: designated as SLLN11) to inhibit breast cancer metastasis to the lung by more than 50% at a dose of 30 mg/kg and below given bi-weekly for 3 weeks. Moreover, compound 4 was also able to inhibit pancreatic cancer cell (Mia-PaCa) and renal adenocarcinoma cell (RENCA) growth in vivo. A highthroughput kinase screening combined to biochemical assays identified the primary targets of compound 4 as Aurora A kinase (IC50=3.8 nM) and PKC-alpha kinase (IC50=10.9 nM). These kinases are directly involved in pathways controlling cell differentiation programs, metastasis signaling, as well as EMT and CSC programming and their overexpression was reported to predict decreased metastasis-free survival.

Figure 1B:
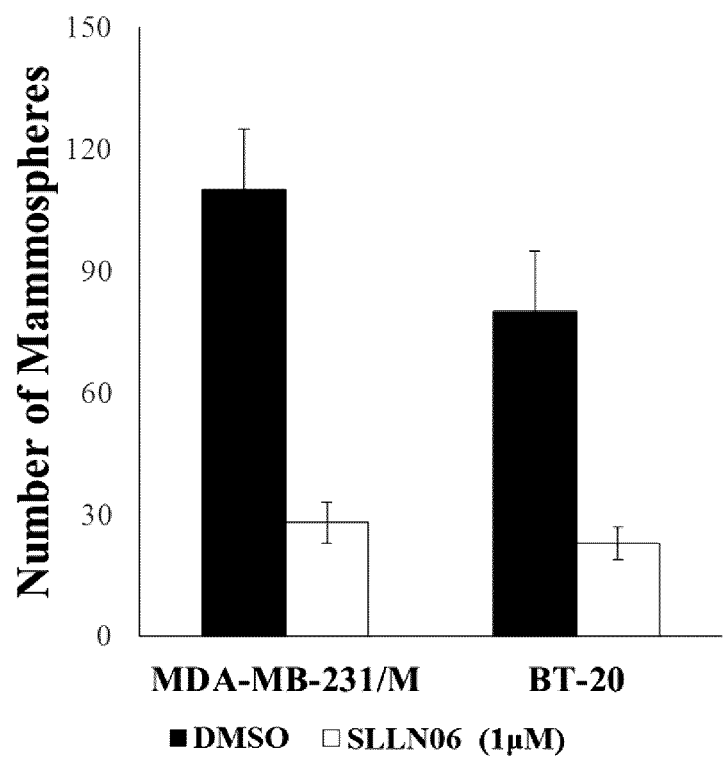

Cell Culture:
Cancer cell lines: MDA-MB-231, BT-20, Panc-1, OVCAR-3, 4T1 and RENCA were obtained from ATCC. Epithelial breast adenocarcinoma cell line PMC42-LA, were kindly provided by Dr. Ackland. Mia-Paca cells were kindly provided by Dr. George Zogopoulos. All cancer cell lines were cultured in RPMI1640x with 10% fetal bovine serum with 1% penicillin/streptomycin, and maintained at 37° C. in 5% atmosphere of $CO_2$. In the case of growth factor stimulation, cells were serum starved for no longer than 12H, and then stimulated with 20 ng/ml EGF for 40 minutes.
Cell Cycle Analysis
Cell cycles were synchronized prior to treatment through overnight serum deprivation. After treatment, cells were fixed and permeabilized using BD Cytofix/Cytoperm reagent (BD Bioscience), washed with PBS, and treated with 100 μg/ml Bovine Pancreas RNase A (US Biological). Cells were then stained with 25 μg/ml propidium iodide (Sigma) for 15 minutes and then immediately analyzed by flow cytometry using BD FACScalibur. The data was analyzed using FCS Express software.
In Vitro Inhibition of Organoid Differentiation and Tumorsphere Formation
Colony Formation Assay
After treatment with 1 μM Compound 1 for 72H, MDA-MB-231 and BT-20 cells were digested with 0.25% trypsin and reseeded at $2.5×10^4$ cells/ml in 60 mm Ultralow Adherence plates (Corning) in DMEM/F12 supplemented with 5 ug/ml human insulin, 20 ng/ml human epidermal growth factor, 0.5 ug/ml hydrocortisone and 2% B27 (Invitrogen). Tumorspheres were then visualized (FIG. 1A) and then quantified (FIG. 1B). An important feature of cancer stem-like cells is their enhanced tumorsphere forming potential when grown in suspension. The tumorsphere forming capacity of Compound 1-treated MDA-MB-231 and BT-20 were analyzed in FIG. 1A. Consistent with previous characterization of these cells, in the absence of Compound 1, both MDA-MB-231 and BT-20 are capable of propagating as small individual tumorspheres that survive passaging. On the other hand, FIGS. 1A and B show that Compound 1 induces a dramatic reduction in viable tumorspheres.

Figure 1C:
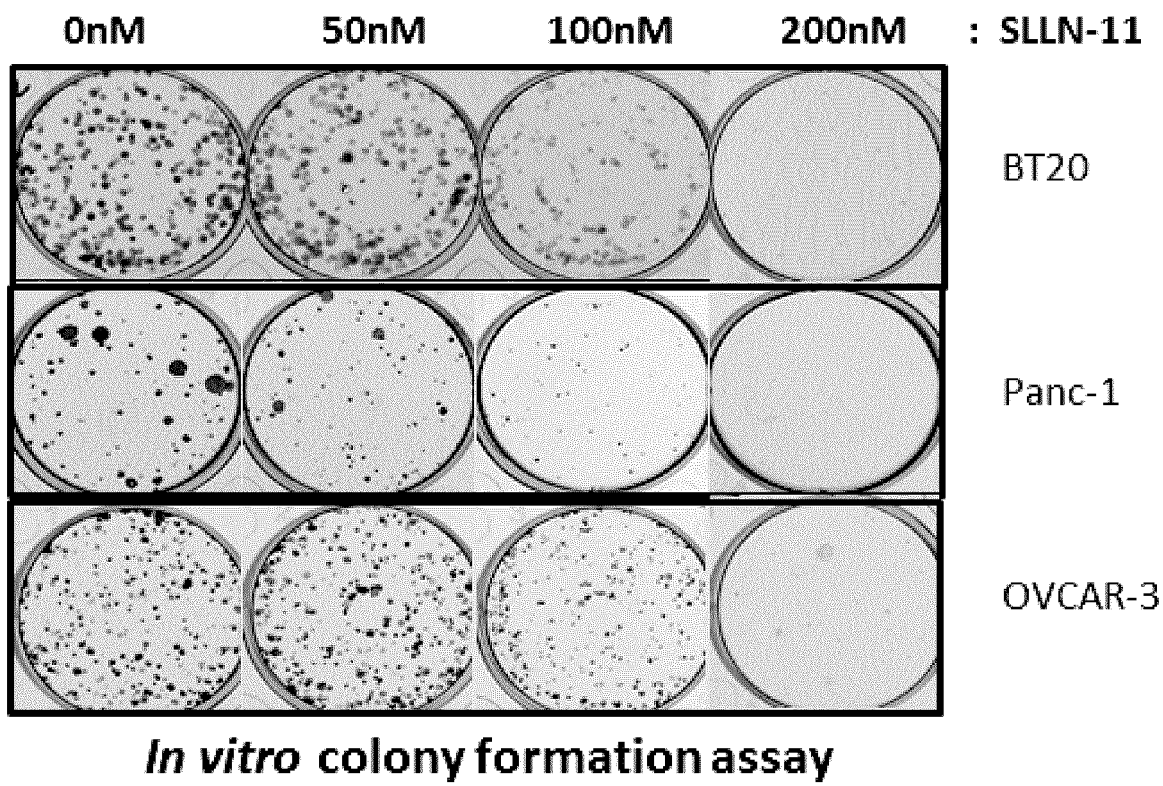
FIG. 1C is a photograph of cancer cell colonies, growing in culture after using a control or a compound of this description.

Clonogenic assays were also performed using standard techniques as previously described. Briefly, cells were harvested from exponential-phase cultures, counted and plated at densities of 200 cells per well of a 12-well plate. Twenty-four hours after plating, the compounds were delivered once at the mentioned concentration. Negative control was carried out by treating the cells with DMSO. After 6 days of incubation in the presence of the compounds, the cells were stained with 0.5% crystal violet in absolute ethanol, and colonies were counted using the machine GelCount™ Tumor Colony Counter from Oxford Optronix Ltd. Each experiment was done in triplicates. Significant reduction in the colony forming abilities of BT20, Panc-1 and OVCAR-3 cells was observed in the presence of compound 4 (FIG. 1C).

Figure 2:
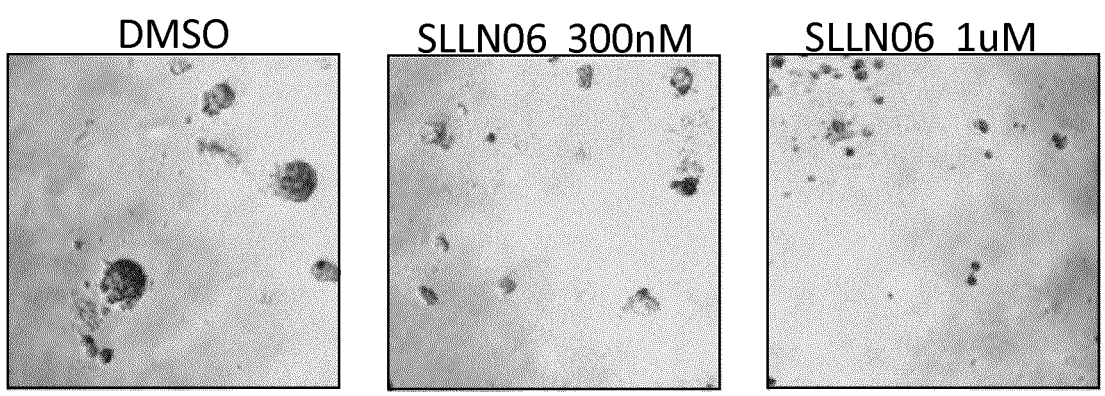
FIG. 2 represents the photomicrograph of the number of organoids growing in culture after using a control or a compound of this description.

In order to confirm that the reduction of CSC markers by Compound 1 correlates with loss of stem-cell properties, the effect of Compound 1 was investigated on the differentiation capability of a well-established PMC42-LA breast cell line. PMC42-LA cells treated with the appropriate concentrations of Compound 1 were also plated on Compound 1 containing matrigel and allowed to form organoids. Since the defining characteristic of stem cells is pluripotency—the capacity of a cell to differentiate into varying progenies, then Compound 1 may inhibit the differentiation process in those PMC42-LA cells. In the absence of drug treatment, PMC42-LA cells undergo differentiation into secretory organoids when cultured on matrigel. The results show that exposure to Compound 1 did not reduce the number of overall colonies but visibly prevented the differentiation and expansion of these colonies into larger organoid structures (FIG. 2).

Therefore, our results demonstrate that Compound 1 inhibits stem-like characteristics.

Induction of Aberrant Cell Division

It was observed during Compound 1 treatment that the targeting effect against stem-like cells is visibly associated with morphological changes resembling cell polyploidization, the accumulation of multiple DNA copies in a cell. This biological phenomenon sometimes occur as part of cell differentiation and is often associated with disruption of normal cell cycle. The identification of Aurora kinases (described below) as targets of Compound 1 supports the possible impact on cell division. Therefore the effect of Compound 1 on cell cycle using FACS analysis to measure propidium iodide staining was investigated.

The obtained results confirmed that Compound 1 induces a dose-dependent accumulation of polyploidic cells.

High-Throughput Kinase Assay

Figure 3:
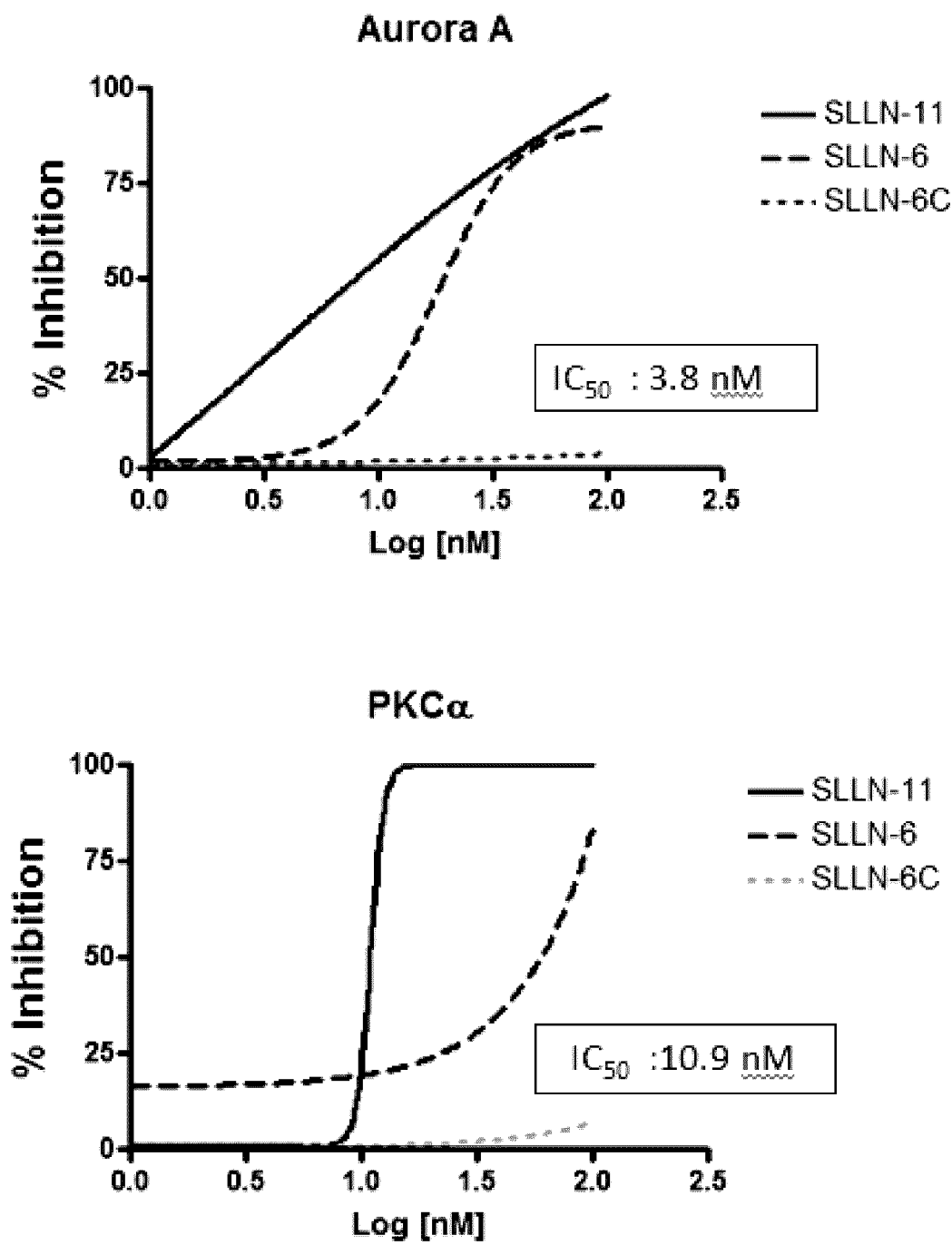
FIG. 3 are the graphical representations of the titration curve of Aurora A and protein kinase C α of a control or a compound of this description.

Screening of Compounds 1-4 against several kinases identified two prominent targets of these compounds as the Aurora A kinase and calcium dependent protein kinase C isoforms α, βI, βII and τ (Tables 1 to 3). IC50s for these two targets were obtained by plotting inhibition levels at 500 nM, 100 nM, 50 nM and 10 nM (FIG. 3). These kinases are directly involved in pathways controlling cell differentiation programs, metastasis signaling, as well as EMT and CSC programming and their overexpression was reported to predict decreased metastasis-free survival.

TABLE 1

Percent inhibition of kinase activity in vitro by compounds 1-3 at 500 nM.

| Kinase | SLLN-6 (500 nM) | SLLN-7 (500 nM) | SLLN-8 (500 nM) |
|---|---|---|---|
| AKT1 (PKB alpha) | 11 | 15 | 29 |
| AURKA (Aurora A) | 94 | 97 | 99 |
| AURKB (Aurora B) | 25 | 13 | 19 |
| AURKC (Aurora C) | 10 | 11 | 7 |
| BRAF-ZLYTE-100 | not tested | not tested | not tested |
| EEF2K | 11 | 11 | 5 |
| EGFR (ErbB1) | 0 | 0 | 0 |
| ERBB2 (HER2) | 0 | 0 | 2 |
| FGFR1 | 2 | 0 | 13 |
| FLT1 (VEGFR1) | 1 | 5 | 7 |
| FRAP1 (mTOR) | 2 | 5 | 1 |
| IGF1R | 12 | 11 | 13 |
| JAK2 | 10 | 13 | 11 |
| LCK | 14 | 14 | 16 |
| MET (cMet) | 10 | 5 | 17 |
| PDGFRA (PDGFR alpha) | 3 | 4 | 5 |
| PIK3CA/PIK3R1 | 61 | 62 | 53 |
| PRKCA (PKC alpha) | 98 | 96 | 86 |
| PRKCB1 (PKC beta I) | not tested | not tested | not tested |
| PRKCB2 (PKC beta II) | not tested | not tested | not tested |
| PRKCD (PKC delta) | not tested | not tested | not tested |
| PRKCE (PKC epsilon) | not tested | not tested | not tested |
| PRKCG (PKC gamma) | not tested | not tested | not tested |
| PRKCH (PKC eta) | not tested | not tested | not tested |
| PRKCI (PKC iota) | not tested | not tested | not tested |
| PRKCQ (PKC theta) | not tested | not tested | not tested |
| PRKCZ (PKC zeta) | not tested | not tested | not tested |
| PRKD1 (PKC mu) | not tested | not tested | not tested |
| PTK2 (FAK) | 7 | 7 | 8 |
| RAF1 (cRAF) Y340D Y341D | 4 | 0 | 10 |
| RET | 23 | 18 | 36 |
| SRC | 5 | 7 | 7 |
| SYK | 8 | 9 | 24 |
| TGFBR1 (ALK5) | 0 | 0 | 0 |
| YES1 | 47 | 35 | 53 |

TABLE 2

Percent inhibition of kinase activity in vitro by the comparative compound 6C and compounds 1-4 at 100 nM.

| Kinase | SLLN-6C (100 nM) | SLLN-6 (100 nM) | SLLN-7 (100 nM) | SLLN-8 (100 nM) | SLLN-11 (100 nM) |
|---|---|---|---|---|---|
| AKT1 (PKB alpha) | 2 | 4 | 4 | 1 | 4 |
| AURKA (Aurora A) | 4 | 89 | 93 | 78 | 95 |
| AURKB (Aurora B) | 10 | 12 | 19 | 24 | 14 |
| AURKC (Aurora C) | 0 | 2 | 0 | 0 | 0 |
| BRAF-ZLYTE-100 | 1 | 1 | 0 | 0 | 0 |
| EEF2K | 1 | 7 | not tested | not tested | 10 |
| EGFR (ErbB1) | 4 | 1 | not tested | not tested | 0 |
| ERBB2 (HER2) | not tested | not tested | not tested | not tested | not tested |
| FGFR1 | 0 | 0 | not tested | not tested | 0 |
| FLT1 (VEGFR1) | 0 | 0 | not tested | not tested | 4 |
| FRAP1 (mTOR) | 0 | 1 | not tested | not tested | 8 |
| IGF1R | 0 | 0 | not tested | not tested | 4 |
| JAK2 | 7 | 10 | 15 | 13 | 18 |
| LCK | 8 | 7 | 10 | 0 | 8 |
| MET (cMet) | 0 | 2 | 1 | 0 | 4 |
| PDGFRA (PDGFR alpha) | 0 | 0 | not tested | not tested | 1 |
| PIK3CA/PIK3R1 | 0 | 0 | 0 | 12 | 0 |
| PRKCA (PKC alpha) | 0 | 83 | 84 | 45 | 98 |
| PRKCB1 (PKC beta I) | not tested | not tested | not tested | not tested | not tested |
| PRKCB2 (PKC beta II) | not tested | not tested | not tested | not tested | not tested |
| PRKCD (PKC delta) | not tested | not tested | not tested | not tested | not tested |
| PRKCE (PKC epsilon) | not tested | not tested | not tested | not tested | not tested |
| PRKCG (PKC gamma) | not tested | not tested | not tested | not tested | not tested |
| PRKCH (PKC eta) | not tested | not tested | not tested | not tested | not tested |

TABLE 2-continued

Percent inhibition of kinase activity in vitro by the comparative compound 6C and compounds 1-4 at 100 nM.

| Kinase | SLLN-6C (100 nM) | SLLN-6 (100 nM) | SLLN-7 (100 nM) | SLLN-8 (100 nM) | SLLN-11 (100 nM) |
|---|---|---|---|---|---|
| PRKCI (PKC iota) | not tested | not tested | not tested | not tested | not tested |
| PRKCQ (PKC theta) | not tested | not tested | not tested | not tested | not tested |
| PRKCZ (PKC zeta) | not tested | not tested | not tested | not tested | not tested |
| PRKD1 (PKC mu) | not tested | not tested | not tested | not tested | not tested |
| PTK2 (FAK) | 3 | 5 | 5 | 0 | 1 |
| RAF1 (cRAF) Y340D Y341D | not tested | not tested | not tested | not tested | not tested |
| RET | 6 | 5 | 6 | 5 | 10 |
| SRC | 3 | 1 | 4 | 4 | 4 |
| SYK | 2 | 6 | 2 | 0 | 6 |
| TGFBR1 (ALK5) | 0 | 0 | 0 | 3 | 0 |
| YES1 | 5 | 22 | 22 | 17 | 24 |

TABLE 3

Percent inhibition of kinase activity in vitro by the comparative compound 6C and compounds 1 and 4 at indicated concentrations.

| Kinase | SLLN-6C (50 nM) | SLLN-6 (50 nM) | SLLN-11 (50 nM) | SLLN-11 (10 nM) |
|---|---|---|---|---|
| AKT1 (PKB alpha) | not tested | not tested | not tested | not tested |
| AURKA (Aurora A) | not tested | not tested | 87 | 55 |
| AURKB (Aurora B) | not tested | not tested | not tested | not tested |
| AURKC (Aurora C) | not tested | not tested | not tested | not tested |
| BRAF-ZLYTE-100 | not tested | not tested | not tested | not tested |
| EEF2K | not tested | not tested | not tested | not tested |
| EGFR (ErbB1) | not tested | not tested | not tested | not tested |
| ERBB2 (HER2) | not tested | not tested | not tested | not tested |
| FGFR1 | not tested | not tested | not tested | not tested |
| FLT1 (VEGFR1) | not tested | not tested | not tested | not tested |
| FRAP1 (mTOR) | not tested | not tested | not tested | not tested |
| IGF1R | not tested | not tested | not tested | not tested |
| JAK2 | not tested | not tested | not tested | not tested |
| LCK | not tested | not tested | not tested | not tested |
| MET (cMet) | not tested | not tested | not tested | not tested |
| PDGFRA (PDGFR alpha) | not tested | not tested | not tested | not tested |
| PIK3CA/PIK3R1 | not tested | not tested | not tested | not tested |
| PRKCA (PKC alpha) | 14 | 68 | 101 | 22 |
| PRKCB1 (PKC beta I) | 5 | 59 | 95 | not tested |
| PRKCB2 (PKC beta II) | 5 | 62 | 95 | not tested |
| PRKCD (PKC delta) | 0 | 0 | 0 | not tested |
| PRKCE (PKC epsilon) | 4 | 6 | 5 | not tested |
| PRKCG (PKC gamma) | 0 | 45 | 47 | not tested |
| PRKCH (PKC eta) | 0 | 0 | 6 | not tested |
| PRKCI (PKC iota) | 7 | 4 | 7 | not tested |
| PRKCQ (PKC theta) | 0 | 62 | 98 | not tested |
| PRKCZ (PKC zeta) | 9 | 9 | 12 | not tested |
| PRKD1 (PKC mu) | 6 | 5 | 7 | not tested |
| PTK2 (FAK) | not tested | not tested | not tested | not tested |
| RAF1 (cRAF) Y340D Y341D | not tested | not tested | not tested | not tested |
| RET | not tested | not tested | not tested | not tested |
| SRC | not tested | not tested | not tested | not tested |
| SYK | not tested | not tested | not tested | not tested |
| TGFBR1 (ALK5) | not tested | not tested | not tested | not tested |
| YES1 | not tested | not tested | not tested | not tested |

Live Cell Locomotion Assay

Cells were seeded at very low density on multi-well chambered coverglass (LabTek, Rochester, N.Y., USA). After starving, cells were stimulated with 10 ng/mL EGF and plated on a heated humidified stage supplied with 5% $CO_2$. Phase contrast time-lapse images were captured every five minutes for three hours by optimized Nipkow spinning disk confocal microscope (WaveFx spinning disk, Quorum Technologies Inc, Guelph, ON, Canada). Cell motility was measured by tracing the cell periphery manually using Volocity software (Perkin Elmer, Waltham, Mass., USA).

Figure 4:
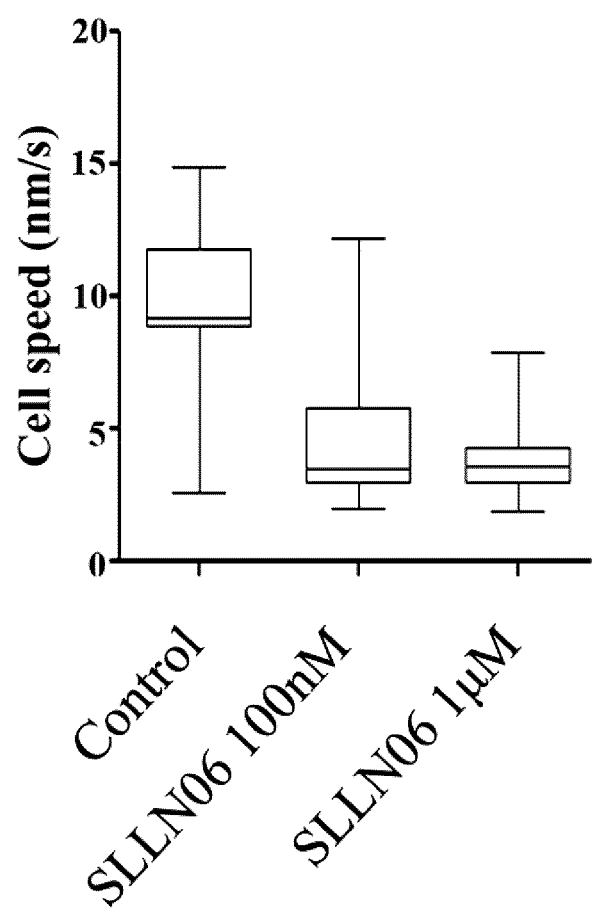
FIG. 4 is the graphical representation of in vitro cell mobility using a control or a compound of this description.

To further confirm Compound 1's anti-metastatic potential, we conducted a live cell locomotion assay to quantify cell movement speed. As shown in FIG. 4, moderate doses of Compound 1 limits the rate of cell mobility by 2-3 fold.

Assessment of In Vivo Distant Metastasis and Primary Tumor Growth of Orthotopically Transplanted Tumor Cells In vivo studies were approved by McGill Animal Care Committee. Cells growing in exponential phase of growth ($1 \times 10^6$ cells/mouse) were transplanted into the mammary fat pad of female SCID (MDA231/M) or Balb/c (4T1) mice. Mia-PaCa cells and RENCA cells were implanted subcutaneously in SCID or Balb/c mice respectively. When primary tumors became palpable mice were randomized and blindly assigned treatment groups. Treatment was given PO for 4 cycles (3 times a week: day 1, day 3, day 5) (n=8-10 mice per condition). Control mice received the vehicle alone (1% DMSO in physiologic solution). A pilot toxicity study confirmed that this schedule using Compound 4 at doses even superior to 30 mg/kg has no apparent toxicity and no body weight loss. Tumor size was measured using a caliper. At the study termination (60-90 days) primary tumors were excised and weighted. The lungs were fixed in 10% Bouin's fixative and lung surface metastases were counted using a stereo-microscope. The number of lung surface metastasis and primary tumor weight were quantified and summarized in Table 4.

TABLE 4

SLLN11 (Compound 4) inhibits in vivo distant metastasis and primary tumor growth.

| | Inhibition of distant metastasis (% control) | Primary tumor weight (g) (% inhibition vs. control) | |
|---|---|---|---|
| | SLLN11 | Vehicle | SLLN11 |
| 4T1/M (triple-negative breast cancer) | 75-82% | 2.1 ± 0.39 | 0.5 ± 0.10 |
| MDA-231/M (human triple-negative breast cancer) | 45-61% | 0.5 ± 0.13 | 0.2 ± 0.08 |
| Mia-PaCa (human pancreatic carcinoma) | Not tested | 1.2 ± 0.18 | 0.6 ± 0.14 |
| RENCA (renal adenocarcinoma) | Not tested | — | (34-55%) |

The results show that all four cell lines responded to treatment with reduced primary tumor growth and less distant metastasis.

The invention claimed is:
1. A compound of formula

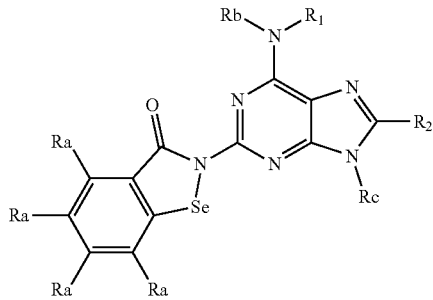

or a pharmaceutically acceptable salt or solvate thereof; wherein
each Ra is H, or a straight or branched alkyl;
Rb is H or a lower straight or branched alkyl;
Rc is H or a lower straight or branched alkyl;
$R_1$ is an optionally substituted selenium-containing heterocycle, an optionally substituted bridged bicycloalkyl or an optionally substituted cycloalkyl, wherein said optional substituent is an alkyl group, wherein said selenium-containing heterocycle is a 5 to 6 membered saturated monocyclic ring consisting of one or two selenium (Se) atoms as the heteroatoms; and
$R_2$ is H or alkyl.

2. The compound of claim 1, or a pharmaceutically acceptable salt or solvate thereof; wherein each Ra is independently H, a straight alkyl or fluoroalkyl of 1-3 carbon atoms; or a branched alkyl or fluoroalkyl of 3 carbon atoms.

3. The compound of claim 1, or a pharmaceutically acceptable salt or solvate thereof; wherein Rb is H, methyl, ethyl, n-propyl, or isopropyl.

4. The compound of claim 1, or a pharmaceutically acceptable salt or solvate thereof; wherein Rc is H, methyl, ethyl, n-propyl, isopropyl or trifluoromethyl.

5. The compound of claim 1, or a pharmaceutically acceptable salt or solvate thereof; wherein $R_1$ is an optionally substituted selenium-containing heterocycle, wherein said selenium-containing heterocycle is a 5 to 6 membered saturated monocyclic ring consisting of one or two selenium (Se) atoms as the heteroatoms.

6. The compound of claim 1, or a pharmaceutically acceptable salt or solvate thereof; wherein $R_1$ is an optionally substituted cycloalkyl.

7. The compound of claim 1, or a pharmaceutically acceptable salt or solvate thereof; wherein $R_2$ is H.

8. The compound of claim 1, or a pharmaceutically acceptable salt or solvate thereof; wherein each Ra is independently H, methyl, ethyl, n-propyl, isopropyl, n-butyl, sec-butyl, ter-butyl, or trifluoromethyl; Rb is H; Rc is H; $R_1$ is an optionally substituted selenium-containing heterocycle, an optionally substituted bridged bicycloalkyl, an optionally substituted cycloalkyl of 6 or 7 carbon atoms; and $R_2$ is H, or methyl.

9. The compound of claim 1, or a pharmaceutically acceptable salt or solvate thereof; wherein each Ra is independently H, methyl, ethyl, n-propyl, isopropyl, n-butyl, sec-butyl, ter-butyl, or trifluoromethyl; Rb is H; Rc is H; $R_1$ is an optionally substituted selenium-containing heterocycle, an optionally substituted bridged bicycloalkyl, or a cycloalkyl; and $R_2$ is H.

10. The compound of claim 1, or a pharmaceutically acceptable salt or solvate thereof; wherein each Ra is H; Rb is H; Rc is H; $R_1$ is an optionally substituted cycloalkyl of 3 to 7 carbon atoms; and $R_2$ is H.

11. The compound of claim 1, or a pharmaceutically acceptable salt or solvate thereof; wherein each Ra is H; Rb is H; Rc is H; $R_1$ is an optionally substituted 5 or 6 membered saturated monocyclic ring consisting of one selenium atom as the heteroatom; and $R_2$ is H.

12. The compound of claim 1, or a pharmaceutically acceptable salt or solvate thereof; wherein each Ra is H; Rb is H; Rc is H; $R_1$ is an optionally substituted bicyclo[2,2,1]heptyl or bicyclo[3,1,1] heptyl; and $R_2$ is H.

13. The compound of claim 1, having the formula

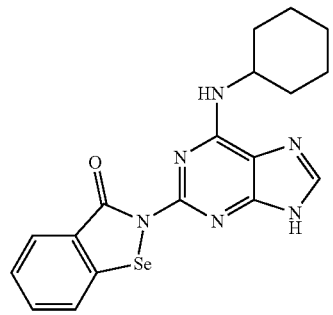

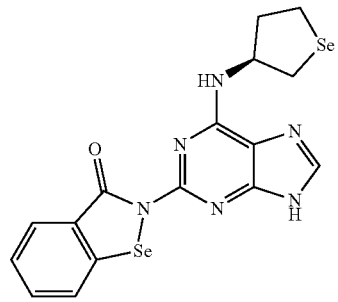

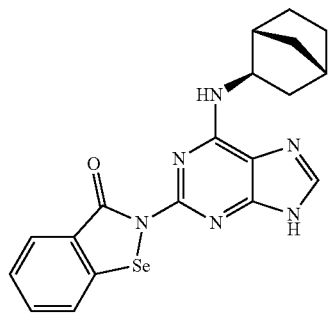

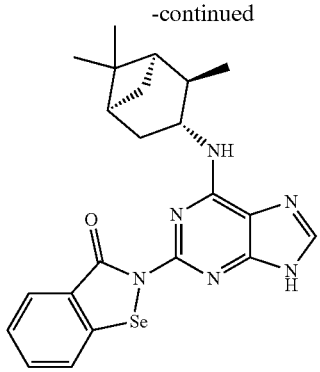

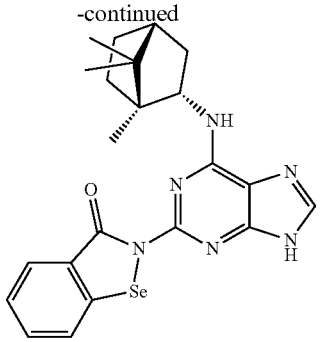

or a pharmaceutically acceptable salt or solvate thereof.

14. A pharmaceutical composition comprising a compound as defined in claim 1, or a pharmaceutically acceptable salt or solvate thereof, and one or more pharmaceutically acceptable carrier and/or excipient.

15. A method for reducing or inhibiting metastasis of metastatic cells in an Aurora A and PKC-alpha kinase-responsive cancer, comprising administering to a patient in need thereof a therapeutically effective amount of a compound or a pharmaceutically acceptable salt thereof as defined in claim 1, and wherein said cancer is triple-negative breast cancer, pancreatic carcinoma or renal adenocarcinoma.

16. The method as defined in claim 15, further comprising administering to a patient in need thereof a therapeutically effective amount of at least one or more therapeutic agents selected from: Alkylating agents, Anti-metabolites, Plant alkaloids and terpenoids, Vinca alkaloids, Podophyllotoxin, Taxanes, Topoisomerase inhibitors, and Cytotoxic antibiotics.

* * * * *